(12) United States Patent
Choi et al.

(10) Patent No.: US 10,624,926 B2
(45) Date of Patent: Apr. 21, 2020

(54) LUTERIAL AND METHOD FOR ISOLATING AND CULTURING THE SAME

(71) Applicant: LUTERION CO., LTD., Gyeonggi-do (KR)

(72) Inventors: Won Cheol Choi, Gyeonggi-do (KR); Young Ah Kwon, Seoul (KR); Suk Hoon Choi, Seoul (KR); Chang Hoon Choi, Seoul (KR)

(73) Assignee: LUTERION CO., LTD., Gyeonggi-Do (KR)

( * ) Notice: Subject to any disclaimer, the term of this patent is extended or adjusted under 35 U.S.C. 154(b) by 387 days.

(21) Appl. No.: 15/109,114

(22) PCT Filed: May 9, 2014

(86) PCT No.: PCT/KR2014/004197
§ 371 (c)(1),
(2) Date: Jun. 29, 2016

(87) PCT Pub. No.: WO2015/108246
PCT Pub. Date: Jul. 23, 2015

(65) Prior Publication Data
US 2016/0324896 A1    Nov. 10, 2016

(30) Foreign Application Priority Data

Jan. 14, 2014    (KR) .................. 10-2014-0004525

(51) Int. Cl.
| G01N 33/48 | (2006.01) |
| A61K 35/19 | (2015.01) |
| A61K 35/12 | (2015.01) |
| C12N 5/078 | (2010.01) |
| C12N 13/00 | (2006.01) |
| G06G 7/58 | (2006.01) |

(52) U.S. Cl.
CPC .............. *A61K 35/19* (2013.01); *A61K 35/12* (2013.01); *C12N 5/0634* (2013.01); *C12N 13/00* (2013.01); *C12N 2529/00* (2013.01)

(58) Field of Classification Search
None
See application file for complete search history.

(56) References Cited

U.S. PATENT DOCUMENTS

| 9,128,101 B2 | 9/2015 | Halbert et al. |
| 2013/0203081 A1 | 8/2013 | Rak et al. |
| 2013/0337440 A1 | 12/2013 | Antes et al. |
| 2014/0162888 A1 | 6/2014 | Kuslich et al. |

FOREIGN PATENT DOCUMENTS

| EP | 3021119 A1 | 5/2016 |
| EP | 3096141 A1 | 11/2016 |
| JP | 05034338 B2 | 5/1993 |
| JP | 05034339 B2 | 5/1993 |
| JP | 2008-505104 A | 2/2008 |
| JP | 2016-526688 A | 9/2016 |
| KR | 100663888 | 12/2006 |
| KR | 10-2013-0056855 A | 5/2013 |
| WO | 2009100029 A1 | 8/2009 |
| WO | 2011127219 A1 | 10/2011 |
| WO | 2013122950 A1 | 8/2013 |
| WO | 2015005553 A1 | 1/2015 |

OTHER PUBLICATIONS

Seeger, H., Blutuntersuchung im Dunkelfeld und ihre Glaubwurdigkeit, URL:https://www.dunkelfeld-blutdiagnostik.de/cms/NS_Blutuntersuchung-im-Dunkelfeld-G 1aubwuerdigkeit.html, Nov. 11, 2007

Seeger, H., Blutuntersuchung im Dunkelfeld und ihre Glaubwurdigkeit, URL:https://www.dunkelfeld-blutdiagnostik.de/cms/NS_Blutuntersuchung-im-Dunkelfeld-G 1aubwuerdigkeit.html, Nov. 11, 2007, Page(s) Machine Translation.

Barry, O., et al., "Mechanisms of Cellular Activation by Platelet Microparticles", "Thrombosis and Haemostasis", Aug. 1999, pp. 794-800, vol. 82.

Barry, O., et al., "Arachidonic Acid in Platelet Microparticles Up-Regulates Cyclooxygenase-2-Dependent Prostaglandin Formation Via a Protein Kinase C/Mitogen-Activated Protein Kinase-Dependent Pathway", "The Journal of Biological Chemistry", Mar. 12, 1999, pp. 7545-7556, vol. 274, No. 11.

(Continued)

*Primary Examiner* — Eric S Dejong
(74) *Attorney, Agent, or Firm* — Hultquist, PLLC; Steven J. Hultquist

(57) ABSTRACT

The present invention relates to blood-derived luterial and a method for isolating and culturing the same. The luterial according to the present invention is a cell or cell-like structure having the following characteristics: (1) it is present in body fluids, including blood, sperm, intestinal juices, saliva, and cellular fluids; (2) it shows a positive staining with Janus green B, Acridine Orange and Rhodamine 123 in an immunofluorescence test; (3) in an optimal environment (pH 7.2-7.4), it has the property of expressing the genes homologous to beta-proteobacteria and gamma-proteobacteria, and has a size of 30-800 nm; (4) in an acidic environment, it has the property of expressing not only the genes homologous to beta-proteobacteria and gamma-proteobacteria, but also eukaryote-derived genes (particularly Streptophyta gene), and grows to a size ranging from 400 nm or more to 2000 nm or more; (5) it is involved in ATP production under normal conditions; and (6) it differs from mitochondria, completely differs from exosomes, and has fusion characteristics corresponding to those of an intermediary between a prokaryote and an eukaryote.

5 Claims, 37 Drawing Sheets

Specification includes a Sequence Listing.

(56) References Cited

OTHER PUBLICATIONS

Lee, Y., et al., "Exosomes and Microvesicles: Extracellular Vesicles for Genetic Information Transfer and Gene Therapy", "Human Molecular Genetics", Aug. 7, 2012, pp. R125-R134, vol. 21, No. 1.
Loke, K., et al., "Potential Role of eNOS in the Therapeutic Control of Myocardial Oxygen Consumption by Ace Inhibitors and Amlodipine", "Cardiovascular Research", 2001, pp. 86-93, vol. 49, No. 1.
Morales-Ruiz, M., et al., "Sphingosine 1-Phosphate Activates AKT, Nitric Oxide Production, and Chemotaxis Through a Gi Protein/Phosphoinositide 3-Kinase Pathway in Endothelial Cells", "The Journal of Biological Chemistry", Jun. 1, 2001, pp. 19672-19677, vol. 276, No. 22.

Rhodamine 123 Positive by Zeiss LSM-780

Real Time Recording(CCD) Mito-tracker Positive (a)　　　　　　　　　(b)　　　　　　　　　(c)

Life Cycling A

Normal (Fission)

Life Cycling B

Abnormal (Fusion or Coagulation)

DAPI / Mitotracker Red / Rhodamine123 Positive
(TCS-SP Leica)

Loading an agarose (1%) gel after qRT-PCR

DNA Isolation, performed by Jun in Boston, 2013 (<100~1200nm)

Fig. 24c

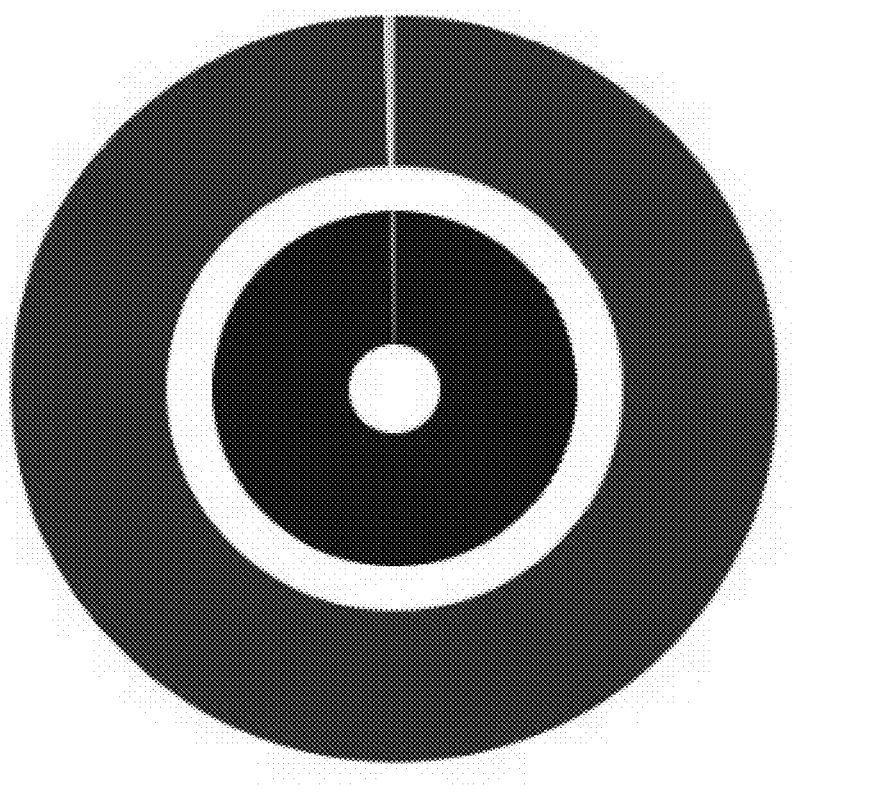

DKU20140414 Fr#3

Phylum
- Proteobacteria(99.67%)
- Firmicutes(0.12%)
- Actinobacteria(0.05%)
- Acidobacteria(0.01%)
- Bacteroidetes(0.14%)
- OD1(0.01%)
- OP3(0.01%)

Family
- Halomonadaceae(99.52%)
- Ralstonia_f(0.02%)
- Moraxellaceae(0.07%)
- Comamonadaceae(0.01%)
- Sphingomonadaceae(0.01%)
- Acetobacteraceae(0.01%)
- Rhodobacteraceae(0.01%)
- Rhodospirillaceae(0.01%)
- Staphylococcaceae(0.02%)
- Streptococcaceae(0.1%)
- Propionibacteriaceae(0.03%)
- EU445199_f(0.01%)
- Chitinophagaceae(0.01%)
- Flavobacteriaceae(0.13%)
- ETC(0.05%)

SEQUENCE LISTING

```
<160> NUMBER OF SEQ ID NOS: 23

<210> SEQ ID NO 1
<211> LENGTH: 51
<212> TYPE: DNA
<213> ORGANISM: Artificial Sequence
<220> FEATURE:
<223> OTHER INFORMATION: Primer, B16S-F

<400> SEQUENCE: 1
cctatcccct gtgtgccttg gcagtctcag acgagtttga tcmtggctca g         51

<210> SEQ ID NO 2
<211> LENGTH: 51
<212> TYPE: DNA
<213> ORGANISM: Artificial Sequence
<220> FEATURE:
<223> OTHER INFORMATION: Primer, Bif16S-F

<400> SEQUENCE: 2
cctatcccct gtgtgccttg gcagtctcag acgggttcga ttctggctca g         51

<210> SEQ ID NO 3
<211> LENGTH: 56
<212> TYPE: DNA
<213> ORGANISM: Artificial Sequence
<220> FEATURE:
<223> OTHER INFORMATION: Primer, B16-7-4

<400> SEQUENCE: 3
ccatctcatc cctgcgtgtc tccgactcag agagctgacw ttaccgcggc tgctgg    56

<210> SEQ ID NO 4
<211> LENGTH: 56
<212> TYPE: DNA
<213> ORGANISM: Artificial Sequence
<220> FEATURE:
<223> OTHER INFORMATION: Primer, B16-7-7

<400> SEQUENCE: 4
ccatctcatc cctgcgtgtc tccgactcag tcagatgacw ttaccgcggc tgctgg    56

<210> SEQ ID NO 5
<211> LENGTH: 56
<212> TYPE: DNA
<213> ORGANISM: Artificial Sequence
<220> FEATURE:
<223> OTHER INFORMATION: Primer, B16-7-8

<400> SEQUENCE: 5
ccatctcatc cctgcgtgtc tccgactcag cgatgagacw ttaccgcggc tgctgg    56

<210> SEQ ID NO 6
<211> LENGTH: 56
<212> TYPE: DNA
```

```
<213> ORGANISM: Artificial Sequence
<220> FEATURE:
<223> OTHER INFORMATION: Primer, B16-7-12

<400> SEQUENCE: 6
ccatctcatc cctgcgtgtc tccgactcag tctgcagacw ttaccgcggc tgctgg        56

<210> SEQ ID NO 7
<211> LENGTH: 56
<212> TYPE: DNA
<213> ORGANISM: Artificial Sequence
<220> FEATURE:
<223> OTHER INFORMATION: Primer, B16-7-13

<400> SEQUENCE: 7
ccatctcatc cctgcgtgtc tccgactcag agcgatgacw ttaccgcggc tgctgg        56

<210> SEQ ID NO 8
<211> LENGTH: 57
<212> TYPE: DNA
<213> ORGANISM: Artificial Sequence
<220> FEATURE:
<223> OTHER INFORMATION: Primer, B16-8-3

<400> SEQUENCE: 8
ccatctcatc cctgcgtgtc tccgactcag atgctgagac wttaccgcgg ctgctgg       57

<210> SEQ ID NO 9
<211> LENGTH: 57
<212> TYPE: DNA
<213> ORGANISM: Artificial Sequence
<220> FEATURE:
<223> OTHER INFORMATION: Primer, B16-8-4

<400> SEQUENCE: 9
ccatctcatc cctgcgtgtc tccgactcag tacagcagac wttaccgcgg ctgctgg       57

<210> SEQ ID NO 10
<211> LENGTH: 57
<212> TYPE: DNA
<213> ORGANISM: Artificial Sequence
<220> FEATURE:
<223> OTHER INFORMATION: Primer, B16-8-18

<400> SEQUENCE: 10
ccatctcatc cctgcgtgtc tccgactcag atcgtgtgac wttaccgcgg ctgctgg       57

<210> SEQ ID NO 11
<211> LENGTH: 57
<212> TYPE: DNA
<213> ORGANISM: Artificial Sequence
<220> FEATURE:
<223> OTHER INFORMATION: Primer, B16-8-21

<400> SEQUENCE: 11
ccatctcatc cctgcgtgtc tccgactcag ctacacagac wttaccgcgg ctgctgg       57

<210> SEQ ID NO 12
<211> LENGTH: 58
<212> TYPE: DNA
<213> ORGANISM: Artificial Sequence
<220> FEATURE:
<223> OTHER INFORMATION: Primer, B16-9-4

<400> SEQUENCE: 12
ccatctcatc cctgcgtgtc tccgactcag cgtgtactga cwttaccgcg gctgctgg     58
```

<210> SEQ ID NO 13
<211> LENGTH: 58
<212> TYPE: DNA
<213> ORGANISM: Artificial Sequence
<220> FEATURE:
<223> OTHER INFORMATION: Primer, B16-9-5

<400> SEQUENCE: 13
ccatctcatc cctgcgtgtc tccgactcag ctgtctacga cwttaccgcg gctgctgg      58

<210> SEQ ID NO 14
<211> LENGTH: 58
<212> TYPE: DNA
<213> ORGANISM: Artificial Sequence
<220> FEATURE:
<223> OTHER INFORMATION: Primer, B16-9-8

<400> SEQUENCE: 14
ccatctcatc cctgcgtgtc tccgactcag agtcactaga cwttaccgcg gctgctgg      58

<210> SEQ ID NO 15
<211> LENGTH: 58
<212> TYPE: DNA
<213> ORGANISM: Artificial Sequence
<220> FEATURE:
<223> OTHER INFORMATION: Primer, B16-9-12

<400> SEQUENCE: 15
ccatctcatc cctgcgtgtc tccgactcag agctcactga cwttaccgcg gctgctgg      58

<210> SEQ ID NO 16
<211> LENGTH: 59
<212> TYPE: DNA
<213> ORGANISM: Artificial Sequence
<220> FEATURE:
<223> OTHER INFORMATION: Primer, B16-10-6

<400> SEQUENCE: 16
ccatctcatc cctgcgtgtc tccgactcag atcacgtgcg acwttaccgc ggctgctgg     59

<210> SEQ ID NO 17
<211> LENGTH: 59
<212> TYPE: DNA
<213> ORGANISM: Artificial Sequence
<220> FEATURE:
<223> OTHER INFORMATION: Primer, B16-10-7

<400> SEQUENCE: 17
ccatctcatc cctgcgtgtc tccgactcag atagctctcg acwttaccgc ggctgctgg     59

<210> SEQ ID NO 18
<211> LENGTH: 59
<212> TYPE: DNA
<213> ORGANISM: Artificial Sequence
<220> FEATURE:
<223> OTHER INFORMATION: Primer, B16-10-8

<400> SEQUENCE: 18
ccatctcatc cctgcgtgtc tccgactcag agtgagctcg acwttaccgc ggctgctgg     59

<210> SEQ ID NO 19
<211> LENGTH: 59
<212> TYPE: DNA
<213> ORGANISM: Artificial Sequence
<220> FEATURE:

```
<223> OTHER INFORMATION: Primer, B16-10-9

<400> SEQUENCE: 19
ccatctcatc cctgcgtgtc tccgactcag agtctgactg acwttaccgc ggctgctgg         59

<210> SEQ ID NO 20
<211> LENGTH: 60
<212> TYPE: DNA
<213> ORGANISM: Artificial Sequence
<220> FEATURE:
<223> OTHER INFORMATION: Primer, B16-11-1

<400> SEQUENCE: 20
ccatctcatc cctgcgtgtc tccgactcag tcatatacgc gacwttaccg cggctgctgg        60

<210> SEQ ID NO 21
<211> LENGTH: 60
<212> TYPE: DNA
<213> ORGANISM: Artificial Sequence
<220> FEATURE:
<223> OTHER INFORMATION: Primer, B16-11-2

<400> SEQUENCE: 21
ccatctcatc cctgcgtgtc tccgactcag tagatagtgc gacwttaccg cggctgctgg        60

<210> SEQ ID NO 22
<211> LENGTH: 60
<212> TYPE: DNA
<213> ORGANISM: Artificial Sequence
<220> FEATURE:
<223> OTHER INFORMATION: Primer, B16-11-3

<400> SEQUENCE: 22
ccatctcatc cctgcgtgtc tccgactcag acgtctctac gacwttaccg cggctgctgg        60

<210> SEQ ID NO 23
<211> LENGTH: 60
<212> TYPE: DNA
<213> ORGANISM: Artificial Sequence
<220> FEATURE:
<223> OTHER INFORMATION: Primer, B16-11-4

<400> SEQUENCE: 23
ccatctcatc cctgcgtgtc tccgactcag ctagagacac tacwttaccg cggctgctgg        60
```

LUTERIAL AND METHOD FOR ISOLATING AND CULTURING THE SAME

CROSS-REFERENCE TO RELATED APPLICATIONS

This application is a U.S. national phase under the provisions of 35 U.S.C. § 371 of International Patent Application No. PCT/KR14/004197 filed May 9, 2014, which in turn claims priority of Korean Patent Application No. 10-2014-0004525 filed Jan. 14, 2014. The disclosures of such international patent application and Korean priority patent application are hereby incorporated herein by reference in their respective entireties, for all purposes.

TECHNICAL FIELD

The present invention relates to luterial which is a mitochondrial-like unidentified nano-sized particle derived from a body fluid and to a method for isolating and culturing the same.

BACKGROUND ART

Micro-substances such as microvesicles in blood have previously been recognized as substance having no special function. However, various experimental data have demonstrated that microvesicles also have biological activity. For example, it was found that platelet-derived microvesicles function to stimulate certain cells through vesicular surface proteins (CD154, RANTES and/or PF-4; Thromb. Haemost. (1999) 82:794; J. Boil. Chem. (1999) 274:7545), and it was reported that physiologically active lipids (e.g., HTET or arachidonic acid) in platelet microvesicles have certain effects on certain target cells (J. Biol. Chem. (2001) 276; 19672; Cardiovasc. Res. (2001) 49(5):88). Thus, because the characteristics (e.g., size, surface antigens, determination of cell-of-origin, payload) of substances such as vesicles present in biological samples, can provide a diagnostic, prognostic or theranostic readout, there remains a need to identify biological markers that can be used to detect and treat disease. Accordingly, there has been an attempt to use RNA and other biological markers associated with vesicles as well as the characteristics of vesicles to provide a diagnosis, prognosis, or theranosis (see WO 2011/127219).

Meanwhile, cancer is a disease in which cells grow abnormally to interfere with the functions of normal cells, and typical examples thereof include lung cancer, gastric cancer (GC), breast cancer (BRC), colorectal cancer (CRC) and the like, but cancer can actually occur in any tissue. In the past, the diagnosis of cancer was based on the external change of biological tissue caused by the growth of cancer cells, but in recent years, it has been attempted to perform diagnosis and detection using trace biomolecules (glycol chain, DNA, etc.) present in blood, biological tissue or cells. However, the cancer diagnostic method that is most commonly used is a diagnostic method that uses either a tissue sample obtained through biopsy or imaging. Biopsy, however, causes great pain in the patient, is costly, and requires a long time for diagnosis of cancer. In addition, if a patient has cancer, the cancer can metastasize during biopsy, and in the case of a site from which a tissue sample cannot be obtained through biopsy, there is a disadvantage in that the diagnosis of disease is impossible before a tissue suspected of having the disease is extracted by a surgical operation. Meanwhile, in diagnosis based on imaging, cancer is diagnosed based on X-ray imaging, nuclear magnetic resonance (NMR) imaging employing an imaging agent having a disease-targeting agent attached thereto, or the like. However, this imaging-based diagnostic method has disadvantages in that an erroneous diagnosis may result from the low skill of a clinical physician or an interpreting physician and in that the method greatly depends on the precision of an imaging device. Furthermore, the imaging-based diagnostic method has a disadvantage in that it is difficult to detect disease in an early stage, because even the most precise device cannot detect a tumor having a size of several mm or less. In addition, the imaging-based diagnostic method has disadvantages in that, because a patient or a person suspected of having disease is exposed to high-energy electromagnetic waves for imaging, which can cause a genetic mutation, the method can cause another disease, and in that the number of diagnoses by imaging is limited.

In other words, biopsy for cancer diagnosis is time-consuming, costly, inconvenient, and causes pain. For this reason, there is a need for a method capable of significantly reducing the number of unnecessary biopsy procedures, as well as a method capable of diagnosing cancer at an early stage.

Under such circumstances, the present inventors found that a disease can be diagnosed and predicted by observing the characteristics of a micro-substance present in a body fluid discharged from a patient. The content of this finding was filed for a patent on Jul. 12, 2013 (Korean Patent Application No. 10-2013-0082060). The present inventors named the unidentified nano-sized particle a "luterial".

However, a technology of efficiently isolating and culturing the micro-substance luterial so as to be capable of being clinically applied has not been known.

Accordingly, the present inventors have developed a method capable of effectively isolating the unidentified nano-sized particle luterial present in a body fluid discharged from a patient or a normal person and have characterized luterial isolated by this method, thereby completing the present invention.

DISCLOSURE OF INVENTION

Technical Problem

It is an object of the present invention to provide a method for isolating and culturing luterial present in a body fluid discharged from a patient or a normal person.

Another object of the present invention is to provide luterial which has integrative characteristics corresponding to those of an intermediary between a prokaryote and an eukaryote, shows a positive fluorescence staining reaction with Janus Green B, Mitotracker Red and Rhodamine 123, is mobile, and has the ability to produce ATP.

Technical Solution

To achieve the above object, the present invention provides a method for isolating luterial, comprising the steps of: separating platelet and blood-derived substances having a size greater than that of platelet from blood; centrifuging the blood fraction obtained after removal of the platelet and the blood-derived substances having a size greater than that of platelet; isolating luterial by collecting a supernatant after the centrifugation; and (4) washing the isolated luterial.

The present invention also provides a method for isolating luterial comprising the steps of: centrifuging a body fluid to provide a supernatant, and filtering the supernatant through a filter having a pore size of 2-5 μm, thereby obtaining a filtered solution; and centrifuging the filtered solution to provide a supernatant, and filtering the supernatant through a filter having a pore size of 0.5-2 μm.

The present invention also provides body fluid-derived luterial having one or more of the following characteristics:

(a) it shows a positive staining reaction with Janus green B, Acridine Orange and Rhodamine 123 in a fluorescence test;

(b) in an optimal environment (pH 7.2-7.4), it expresses beta-proteobacteria-derived and gamma-proteobacteria-derived genes and has a size of 30-800 nm;

(c) in an acidic environment, it expresses not only beta-proteobacteria-derived and gamma-proteobacteria-derived genes, but also eukaryote Streptophyta genes and grows to a size of 400 nm-2000 nm or more;

(d) it is involved in ATP production in normal conditions;

(e) it is a cell or cell-like structure completely different from mitochondria or exosomes;

(f) it is circular or oval in shape in a normal status, and patient-derived luterial has a size (long axis diameter: 800 nm or more) greater than that of normal-status luterial and is mutated to form mutant luterial having a non-uniform morphology;

(g) it has a multiple ring-like membranes and is adherent;

(h) it can be present inside or outside cells;

(i) it is mobile and undergoes fusion and/or fission events;

(j) mutant luterial bursts in a certain condition and has stemness after bursting; and (k) it has a function of regulating p53 gene and telomeres.

The present invention also provides a method for culturing luterial, comprising: adding water to the isolated body fluid-derived luterial; and culturing the luterial at a temperature of 18 to 30° C. under irradiation with IR light.

The present invention also provides an anticancer composite containing luterial as an active ingredient.

BRIEF DESCRIPTION OF THE DRAWINGS

FIG. 10 shows luterial isolated from the cancer patient body fluid. Specifically.

In FIG. 19, the exosome has a size of 20-120 nm, an unclear membrane and a relatively light internal color, and the luterial has a size of 50-800 nm and a distinct membrane or a packed internal structure.

BEST MODE FOR CARRYING OUT THE INVENTION

Figure 1:
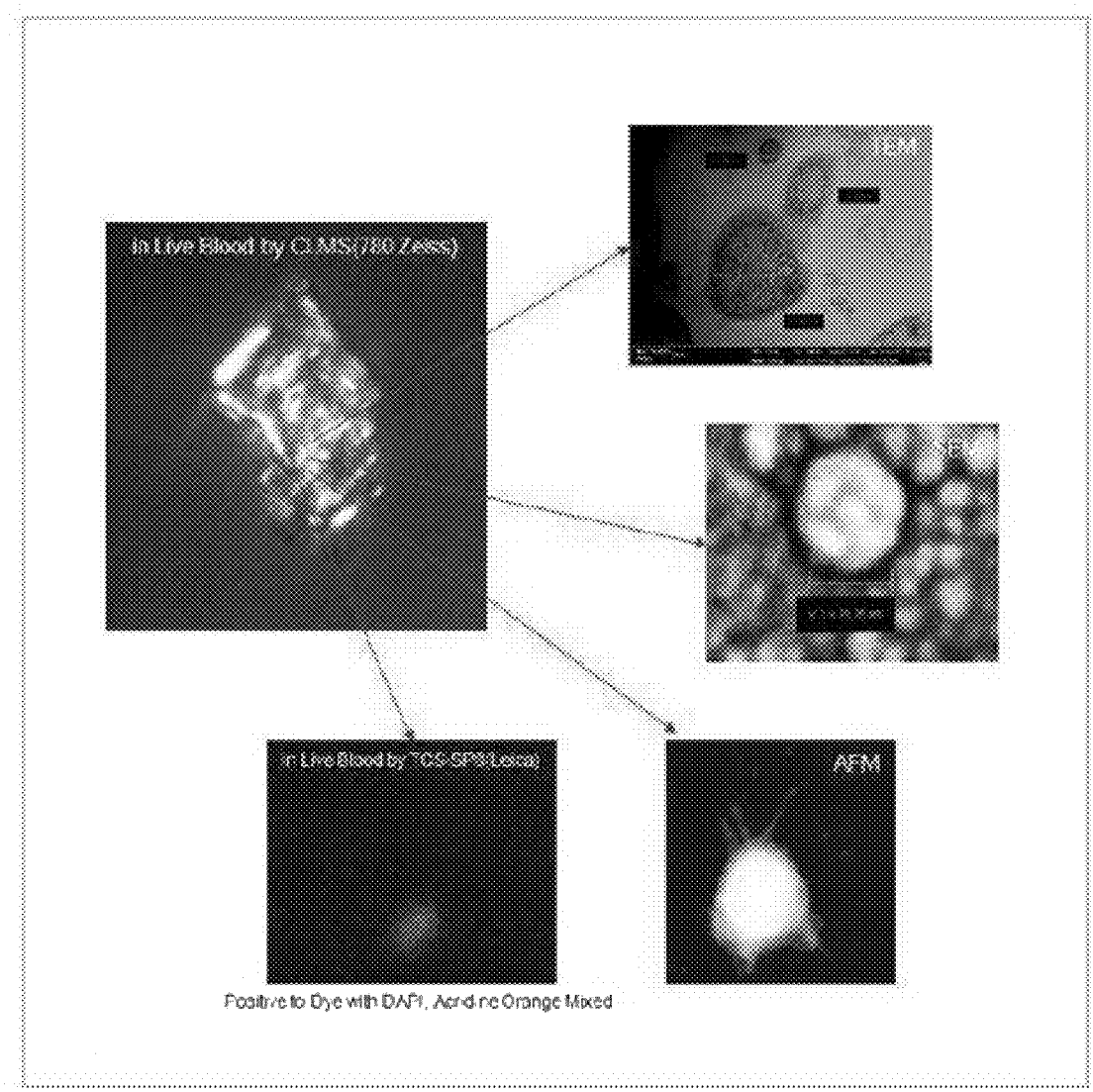
FIG. 1 shows images of the blood-derived unidentified nano-sized particle luterial imaged with a confocal laser scanning microscope (Zeiss), a transmission electron microscope, a scanning electron microscope, an atomic force microscope and a confocal scanner (Leica TCS-SP8).
Figure 2A:
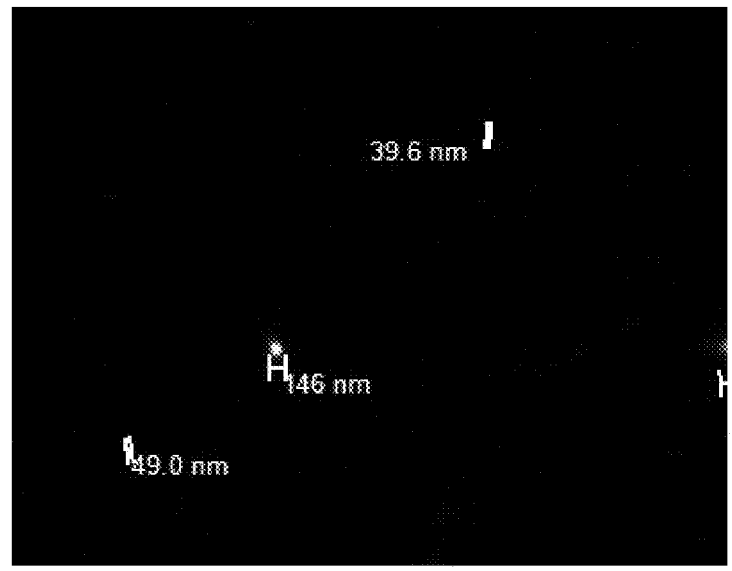
FIG. 2 depicts images showing the shape or morphology of luterial with various sizes ((a): 39.6-49.0 nm, an ultra-high resolution microscope (SR-GSD) image after staining with Mito-tracker Red; (b): 50.1-85.1 nm, an ultra-high resolution microscope (SR-GSD) image after staining with Mito-tracker Red; (c): 76.5 nm, a transmission electron microscope image; (d): 160 nm, a transmission electron microscope image; (e): 170-230 nm, a transmission electron microscope image, a multiple-membrane structure; (f): 234 nm, an image after staining with Janus green B; (g): 250 nm, an atomic force microscope image; (h): 361 nm, a transmission electron microscope image; (i): 650.1 nm, a transmission electron microscope image; and (j): a laser scanning microscope image of luterial having a size of 5 μm or more after staining with DAPI (4',6-diamidino-2-phenylindole).
Figure 2B:
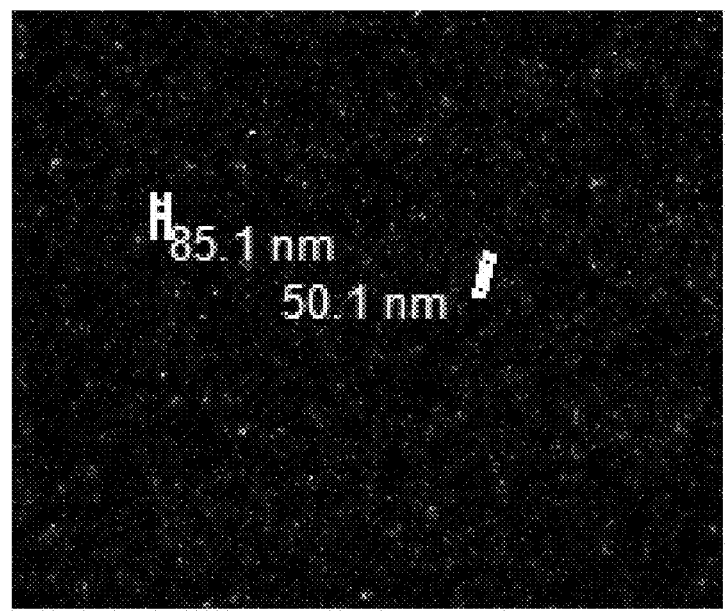
Figure 2C:
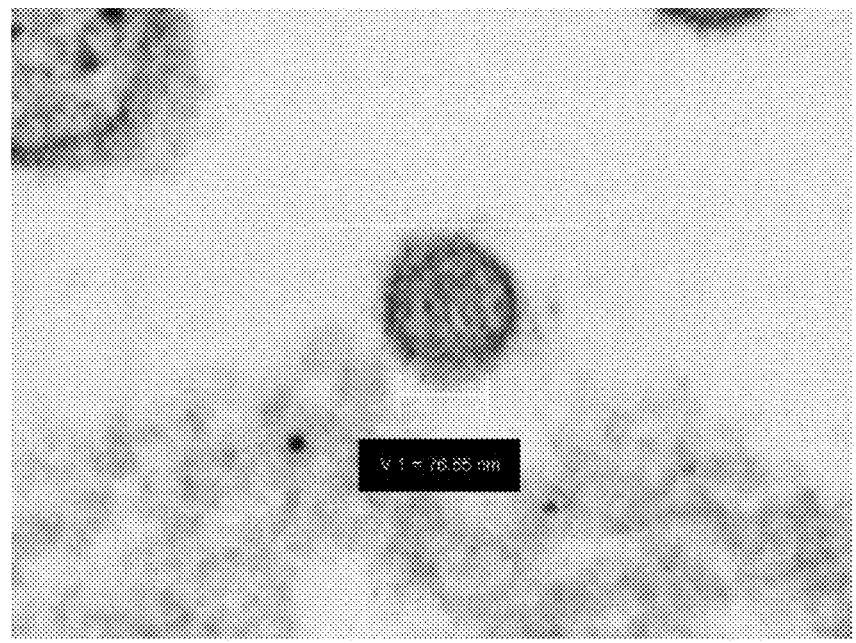
Figure 2D:
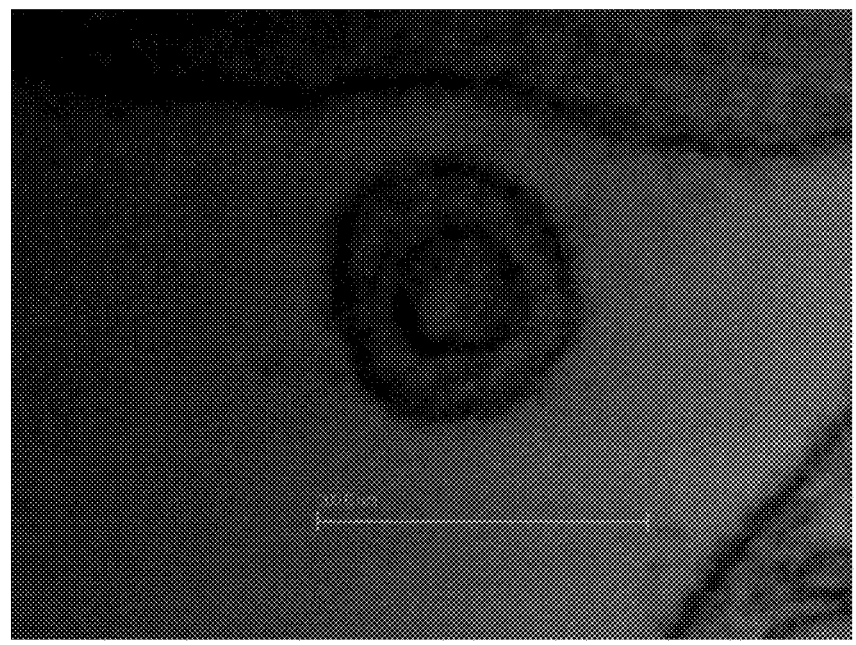
Figure 2E:
Figure 2F:
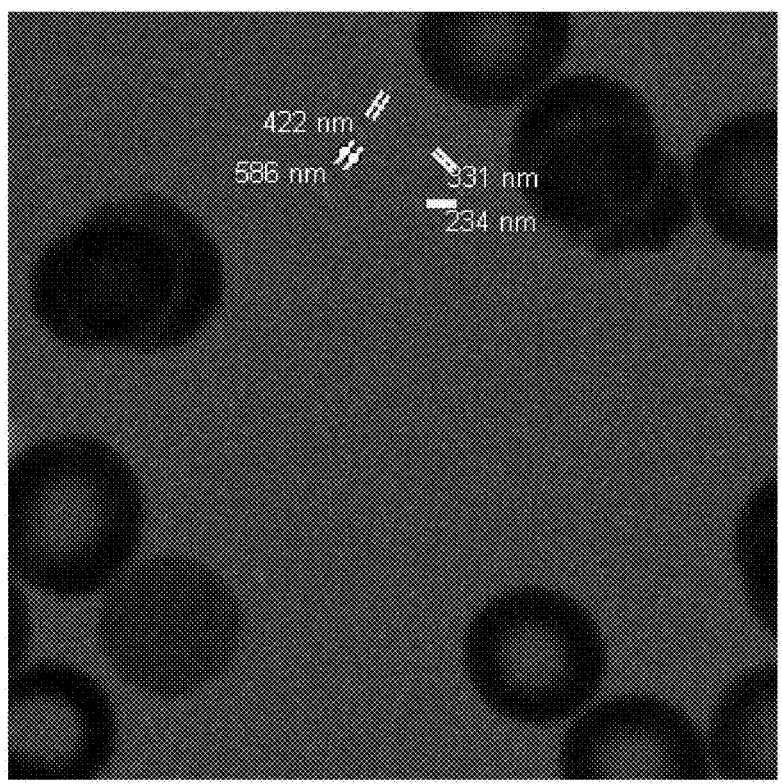
Figure 2G:
Figure 2H:
Figure 2I:
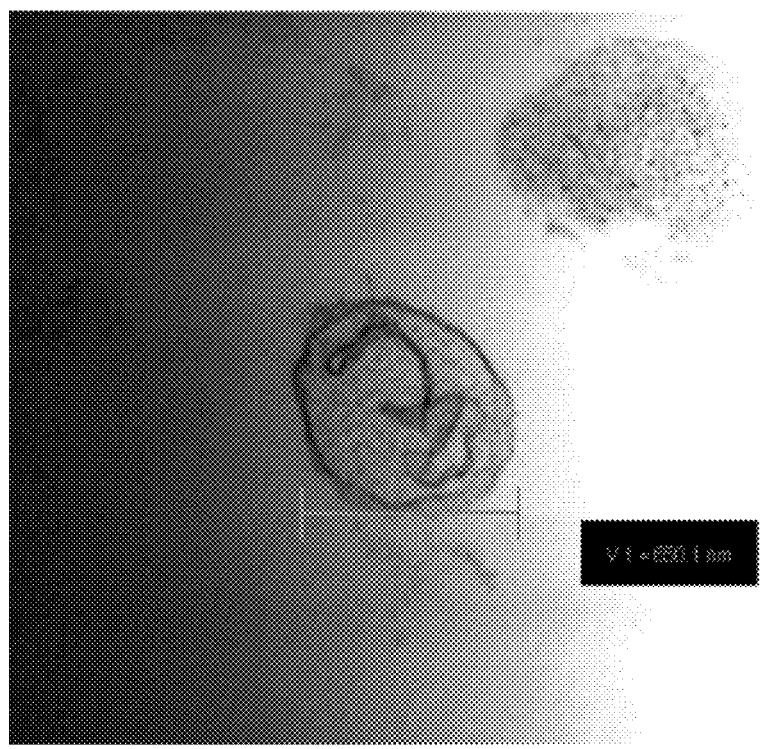
Figure 2J:
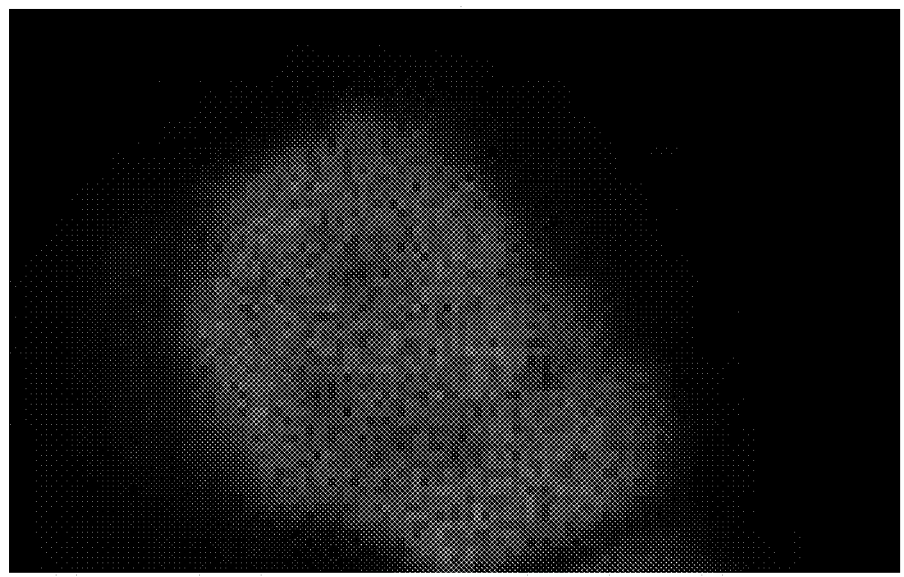
Figure 3:
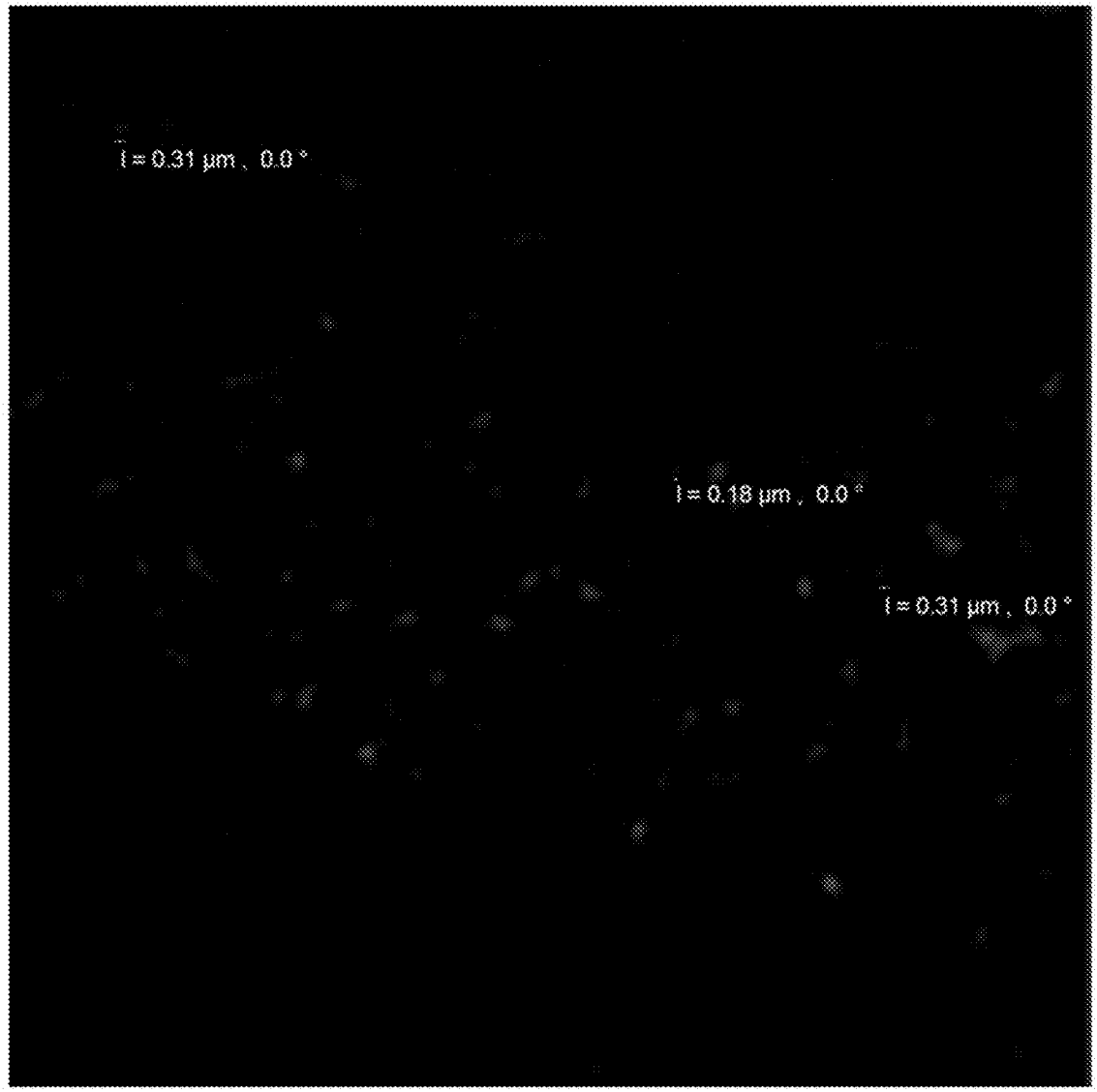
FIG. 3 is an image showing the results of staining luterial with Rhodamine 123 and then observing whether the luterial would be positively stained.
Figure 4:
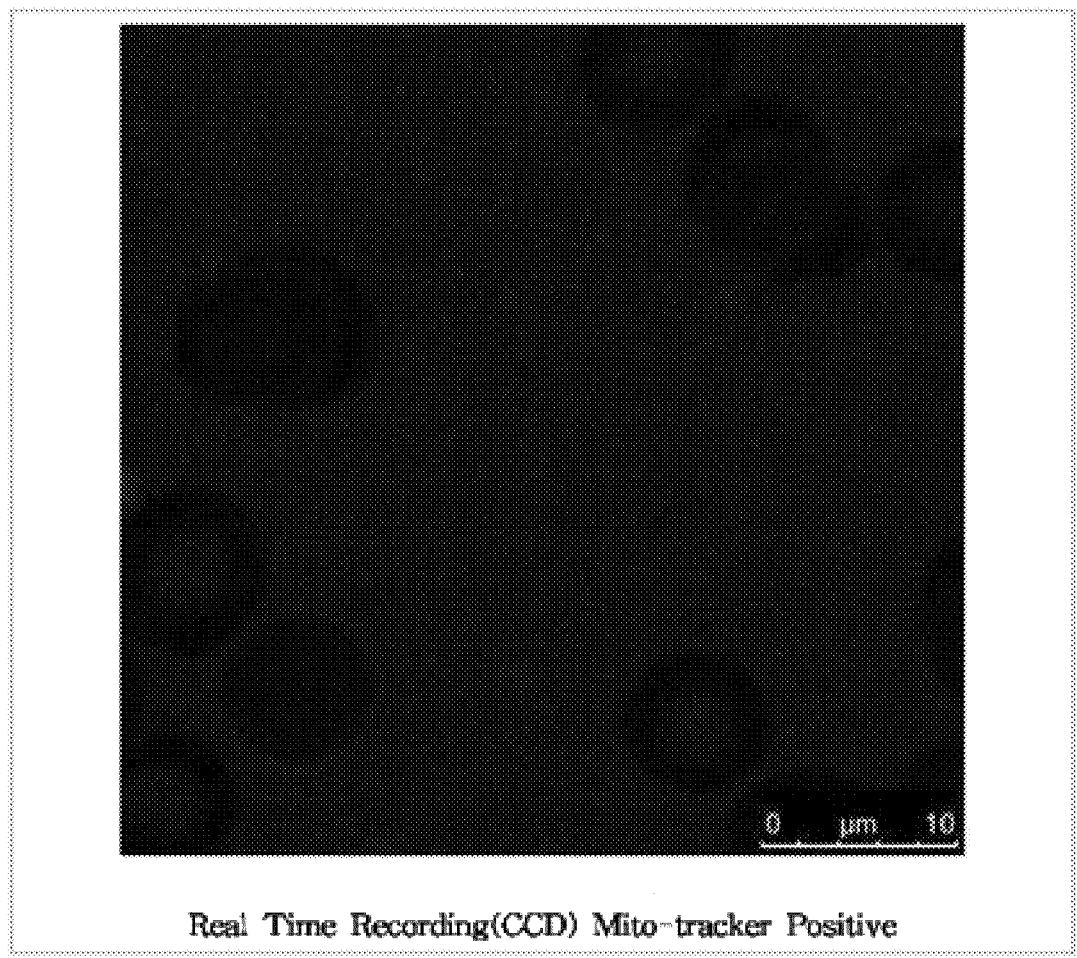
FIG. 4 is an image showing the results of staining luterial with Mito-tracker and then observing whether the luterial would be positively stained.

Unless defined otherwise, all technical and scientific terms used herein have the same meaning as commonly understood by a skilled expert in the field to which the invention pertains. Generally, the nomenclature used herein and the experiment methods, which will be described below, are those well known and commonly employed in the the technical field to which the invention pertains.

As used herein, the term "luterial" named by the present inventors refers to a living organism present in animals and means a fine substance having a size ranging from a size similar to that of virus to about 800 nm (50-800 nm at normal fission stage/800 nm or more at abnormal fusion stage). Luterial has the following characteristics: (1) it is a cell or cell-like structure having integrative characteristics corresponding to those of an intermediary between a prokaryote and an eukaryote; (2) it is present in body fluids, including blood, sperm, intestinal juices, saliva, cellular fluids, etc.; (3) it shows a positive staining reaction with Janus green B, Acridine Orange and Rhodamine 123 in a fluorescence staining test; (4) in an optimal environment (pH 7.2-7.4), it has the property of expressing genes homologous to beta-proteobacteria and gamma-proteobacteria and has a size of 30-800 nm; (5) in an acidic environment, it expresses not only genes homologous to beta-proteobacteria and gamma-proteobacteria, but also eukaryotic genes (particularly Streptophyta genes), and grows to a size of 400-2000 nm or more; (6) it is involved in ATP production under normal conditions; and (7) it is a cell or cell-like structure which differs from mitochondria and completely differs from exosomes. In the case of mammals (including humans), luterial is present in blood, saliva, lymphatic ducts, sperm, vaginal fluids, mother's milk (particularly colostrums), umbilical cord blood, brain cells, spinal cords, and marrow. In addition, in the case of horned animals, luterial is also present in horns.

Normal luterials have a size of 50-800 nm, and mutant luterials formed by fusion have a size of a few tens of micrometers. The term "luterial" may refer to proto mitochondria containing mRNA, miRNA and DNA. Luterial is unique in that it does not dissolve in digestive fluid and infiltrates into blood.

It is expected that luterial will be closely associated with not only signal transduction, cell differentiation and cell death, but also the regulation of cell cycling and cell growth. The present inventors have found that luterial is closely associated with the diagnosis of cancer.

Normal luterial is expected to function to prevent the growth of cancer cells and return cells to a healthy immune state, and the functions thereof are performed by its RNAi (RNA interference) activity that works to normalize genes. When an information system in RNA in the blood of healthy people or animals deviates from a normal status and directs to produce a protein that causes an abnormal disease, luterial will deliberately interfere with the information system so as to inhibit the development of diseases such as cancer. When luterial grows to a size of 200-500 nm or more, it will also be involved in energy metabolism, and when luterial is irradiated with light having a certain wavelength, it will function to amplify light energy in response and will act like chlorophyll. Thus, if luterial does not perform normal functions, it can cause a serious disorder in homeostasis and ATP production and can cause diseases in both respiration and energy metabolism.

Mutant luterials that cannot perform normal functions as described above show phenomena and characteristics different from those of normal luterials and have various sizes or shapes. Specifically, normal luterials ceases to grow after they form double spores, but mutant luterials that are found in the blood of cancer patients or patients with chronic diseases have the property of growing infinitely, similar to stem cells, and thus have a size ranging from 600-800 nm to 200 μm (200,000 nm) or even bigger. In addition, similarly to viruses, luterials show unique characteristics that could enter and grow inside erythrocytes, leukocytes, platelets or the like or aggregate with other luterials.

Thus, it is expected that diseases can be diagnosed or treated by observing the morphological or biochemical characteristics of luterial and thereby promising its wide use in countless applications. However, luterial isolated from body fluids discharged from animals (including humans) is difficult to observe as it quickly disintegrates in vitro or undergoes morphological changes. Furthermore even the normal luterial is changed into mutant luterial within 24 hours under an abnormal environment, making it difficult to accurately diagnose or treat diseases.

In the present invention, the unidentified nano-sized particle luterial present in body fluids isolated from patients or normal people was isolated by two methods.

Therefore, in one aspect, the present invention is directed to a method for isolating luterial from a body fluid.

A first method according to the present invention is a method for isolating luterial from blood, comprising the steps of: (1) separating platelet and blood-derived substances having a size greater than that of platelet from blood; (2) centrifuging the blood after the removal of platelet and the blood-derived substances having a size greater than that of platelet; (3) isolating luterial from a resultant supernatant obtained from centrifugation; and (4) washing the isolated luterial.

Step (1) may comprise a step of passing the blood through a filter having a pore size of 0.8-1.2 μm and removing unfiltered substances. Step (2) may comprise a step of repeatedly centrifuging the blood at 120,000-500,000 g for 5-10 minutes to remove general microvesicles such as exosomes and recovering the supernatant. Step (3) may comprise a step of irradiating visible light to the supernatant obtained by the centrifugation and isolating mobile luterial particles, which are gathered toward light, by pipetting. The blood used in step (1) may be derived from humans among mammals. Luterial is autofluorescent and mobile, and thus luterial particles in the supernatant can be isolated by pipetting the visualized luterial under a dark-field microscope or a confocal microscope with the assistance of irradiation of visible light. Luterial isolated in step (3) may be passed through a filter having a pore size of 50 nm, and an unfiltered portion may be washed out with PBS for isolation of luterial. Because luterial has a long axis diameter of 50 nm or more, blood-derived substances smaller than luterial can be removed by the above-described procedure.

A second method according to the present invention is a method for isolating luterial from a body fluid such as blood or sperm, comprising the steps of: centrifuging the body fluid to provide a supernatant, and filtering the supernatant through a filter having a pore size of 2-5 μm, thereby obtaining a filtered solution; and centrifuging the filtered solution to provide a supernatant, and filtering the supernatant through a filter having a pore size of 0.5-2 μm.

Specifically, the second method may comprise the steps of: centrifuging the body fluid at 2,000-4,000 rpm for 5-30 minutes to provide a supernatant, and filtering the supernatant through a filter having a pore size of 2-5 μm; and centrifuging the filtered solution at 3,000-7,000 rpm for 5-20 minutes, followed by filtration through a filter having a pore size of 0.5-2 μm.

The second method may further comprise a step of irradiating visible light to the filtered solution and isolating mobile luterial particles, which are gathered toward the light, by pipetting. Herein, the luterial is autofluorescent and mobile, and thus luterial particles in the supernatant can be visualized by irradiation with visible light. The isolated luterial may be passed through a filter having a pore size of 50 nm, and an unfiltered portion may be washed out with PBS, thereby obtaining luterial. Because luterial has a long axis diameter of 50 nm or more, blood-derived substances smaller than luterial can be removed by the above-described procedure.

The luterial isolated by each of such two methods can be observed by a dark-field microscope or a confocal microscope, and can be divided according to size into 50-200 nm (developmental phase)/200-400 nm (maturation phase)/400-600 nm (mitosis phase)/600-800 nm (over-mitosis phase) by sequential use of 200 nm, 400 nm, 600 nm, 800 nm and 1000 nm filters.

In the present invention, the isolated luterial was characterized.

(1) Morphology

Figure 12:
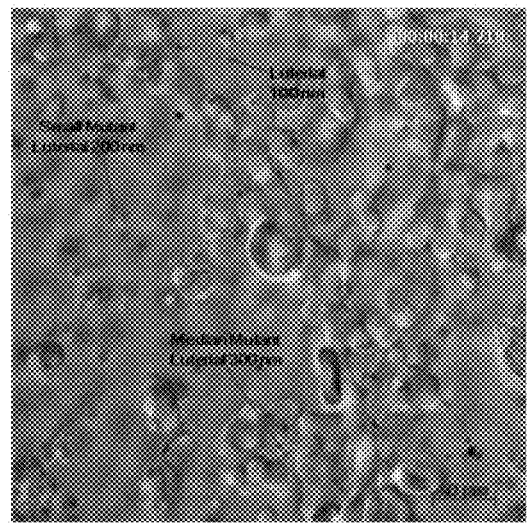
FIG. 12 is an image showing the results of measuring the sizes of luterial and mutated luterial.
Figure 13:
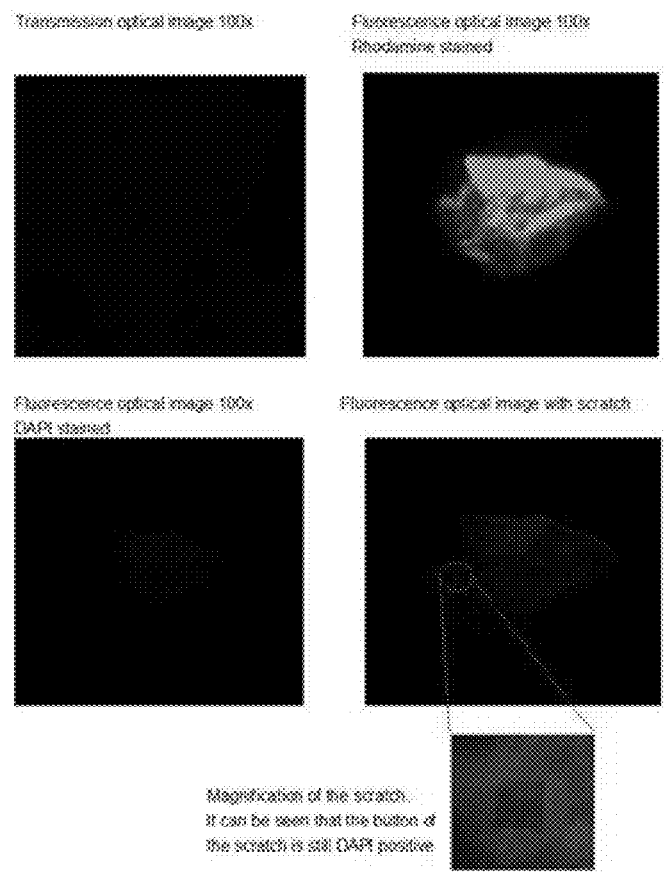
FIG. 13 depicts images showing the results of scratching luterial with an atomic force microscope probe and removing the membrane.
Figure 14A:
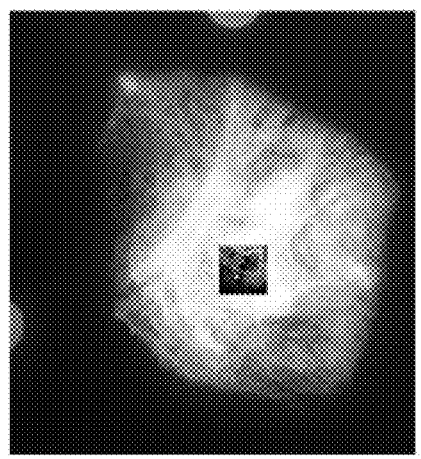
FIGS. 14(a) and 14(b) are atomic force microscope images of mutated luterials that are in a fusion status.
Figure 14B:
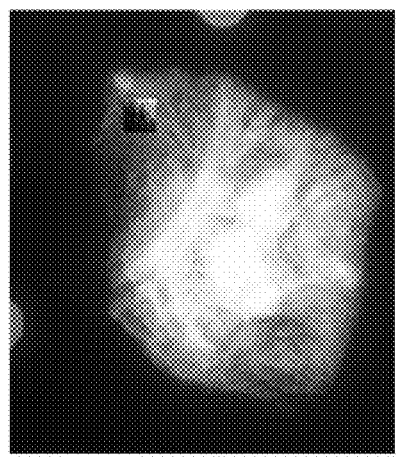
Figure 14C:
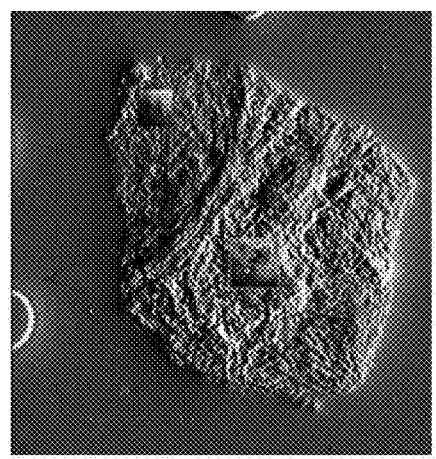
FIGS. 14(c) and 14(d) show the results of imaging the mutated luterials with an atomic force microscope after peeling off the membrane with a cantilever.
Figure 14D:
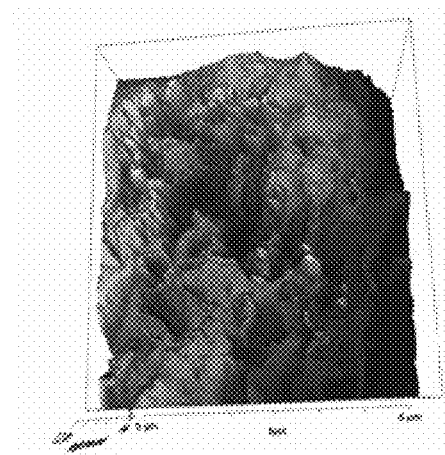
Figure 15:
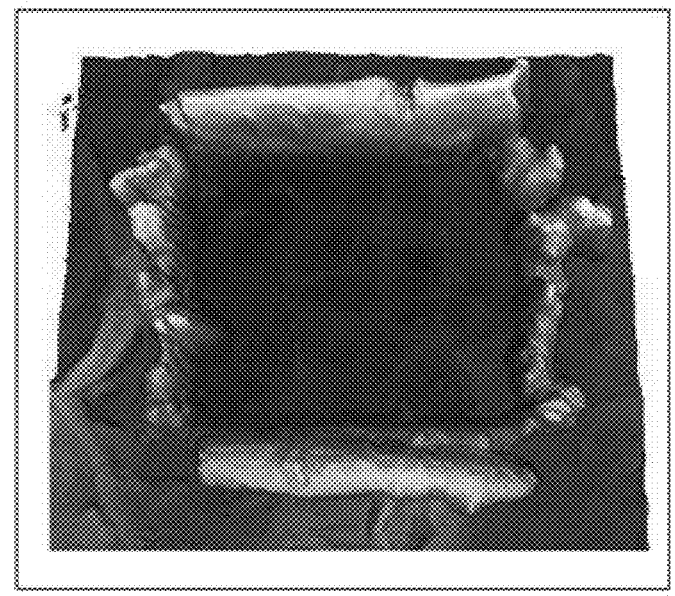
FIG. 15 depicts images showing the results of scratching luterial with an atomic force microscope probe, and then observing DNA through a DAPI-stained image.
Figure 15:
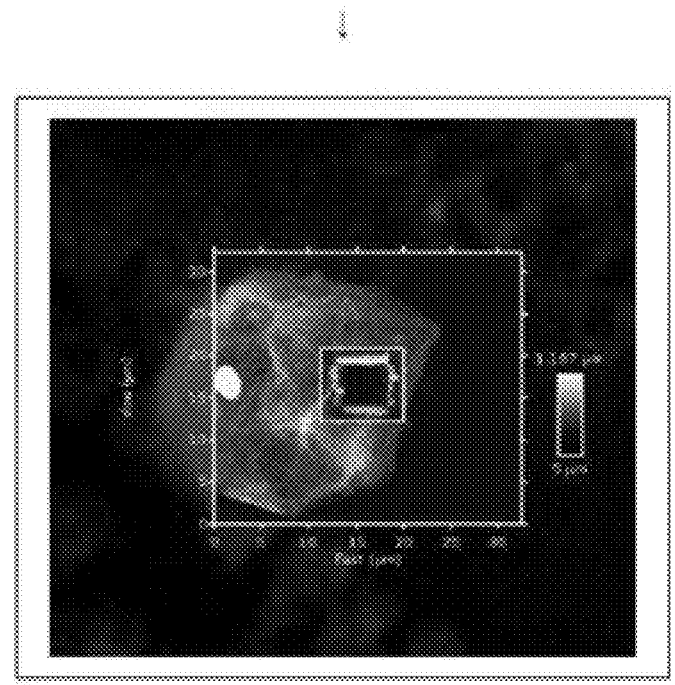

It was found that normal luterials have a size of 50-800 nm (FIGS. 2 and 12), and grow up to a size of 800 nm in the absence of abnormal fusion. The patient-derived luterials have a size (long axis diameter of 800 nm or more) greater than that of healthy person-derived luterials, are mutated to form mutant luterials having a non-uniform morphology, and grow to a size of several thousands of nm when abnormal fusion persists.

In addition, luterial is circular or oval in shape, and shows a multiple ring-like membrane structure in SEM or TEM images, but had no internal cristae structure (FIG. 1).

(2) Fluorescent Staining

It is known that mitochondria are positively stained by Janus green B and fluorescent dyes, including Rhodamine 123, Mitotracker, Acridine Orange, and DAPI, and it was found that luterial is also stained by the same dyes as those for mitochondria. Fluorescence images indicated that the luterial, but not exosomes, showed a reaction similar to that of mitochondria in fluorescent staining test and showed autofluorescence (FIGS. 2(a), 2(b), 2(f) and 2(j), and FIGS. 3 to 6).

(3) Properties

Figure 8:
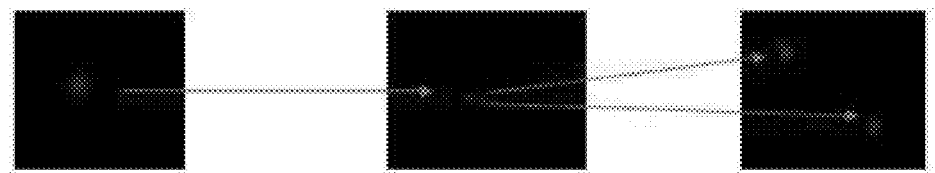
FIG. 8 shows life cycling A of normal luterial and life cycling B of mutated luterial.
Figure 8:
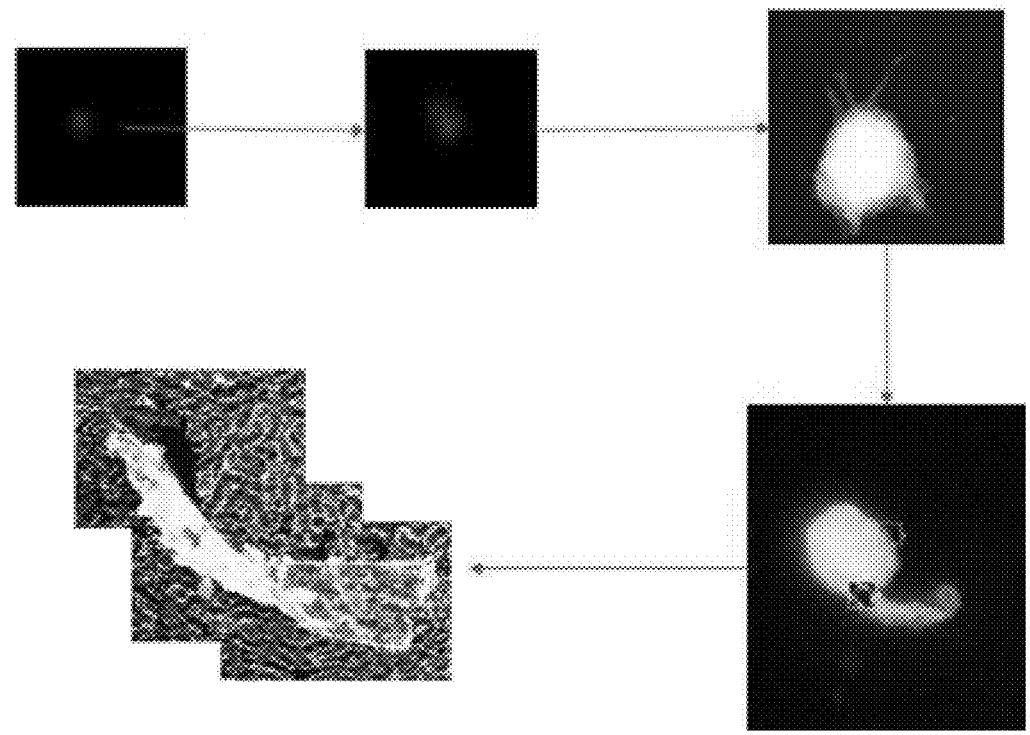
Figure 9:
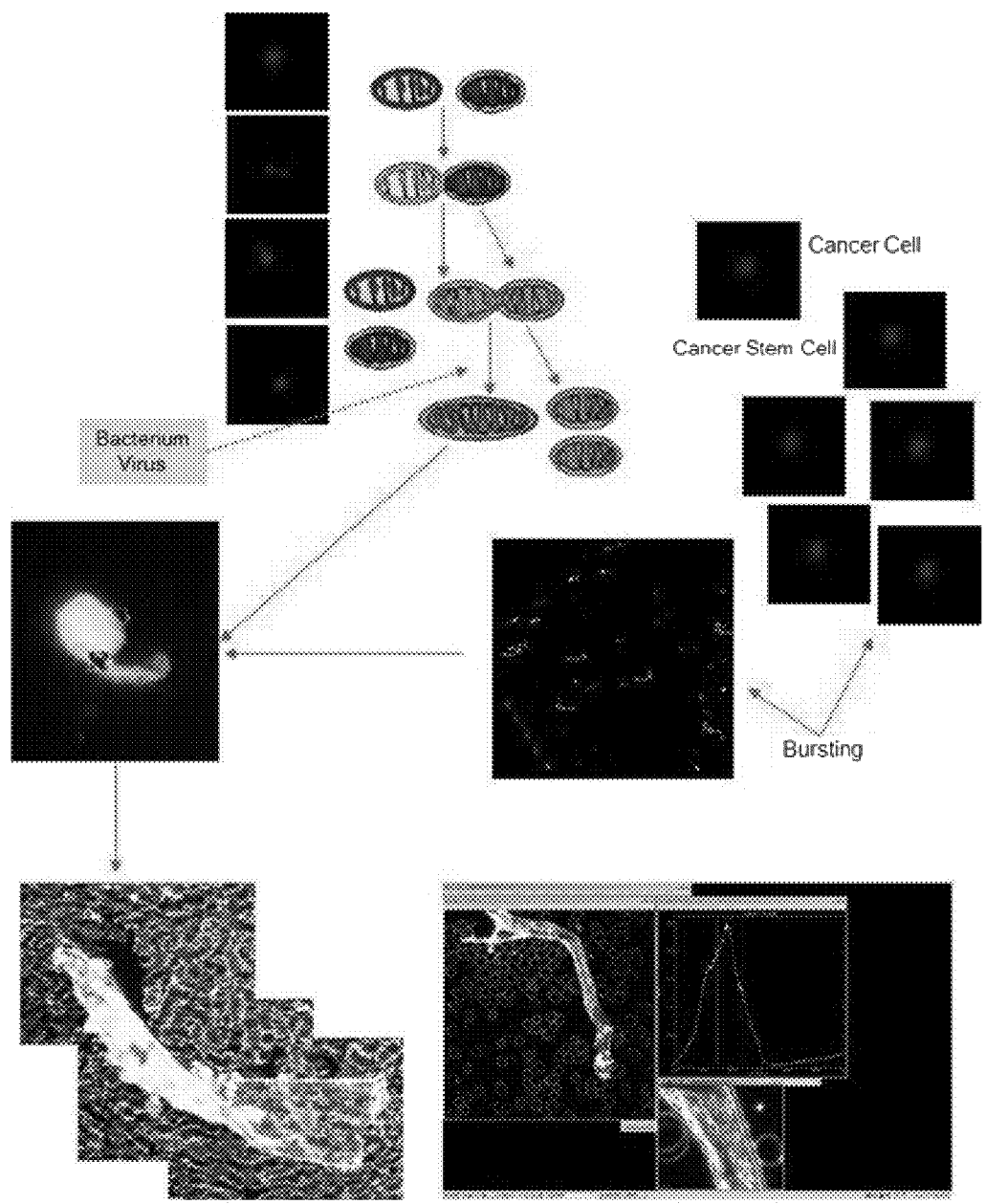
FIG. 9 shows the life cycling and characteristics of mutated luterial.
Figure 11:
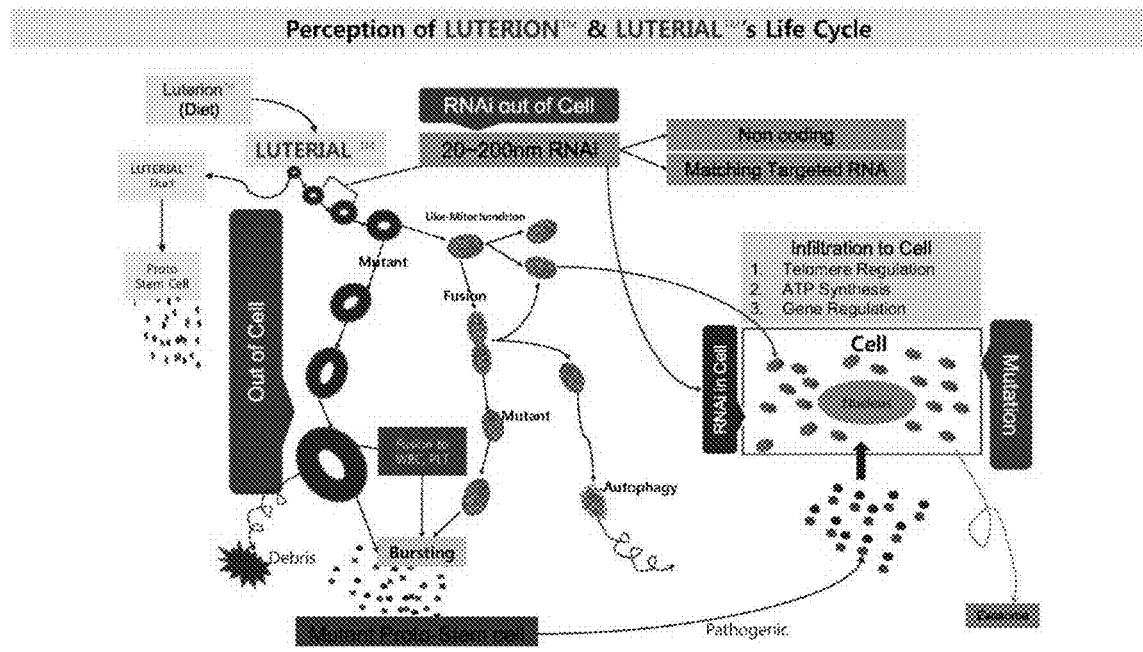
FIG. 11 shows the life cycle of luterial.

Unlike exosomes and microvesicles, luterials were adherent and mobile and underwent fusion or fission events. It was found that mutant luterial did burst under certain conditions, had sternness after bursting, and could be present inside or outside cells (FIGS. 8, 9 and 11).

(4) ATP Production

Figure 18:
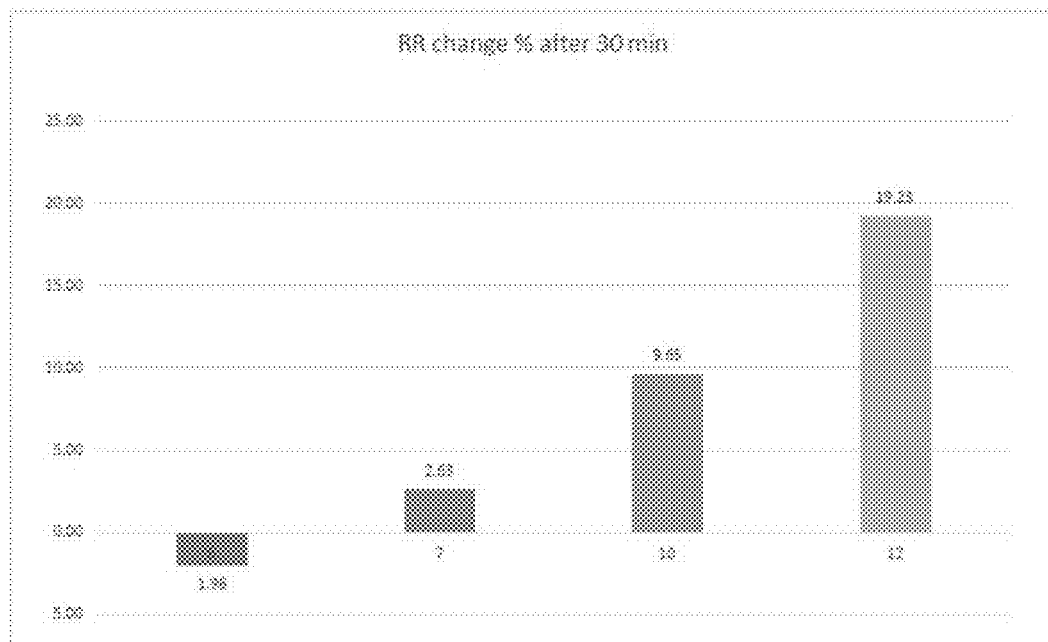
FIG. 18 shows the results of measuring ATP content in media having different luterials added thereto by use of a luciferin-luciferase reaction and a luminometer (SSH: three-star ring; SSF: fisetin; 12 h: activated at 37° C. for 12 hours before an experiment).

ATP production in luterial having a size of 200-400 nm was demonstrated using luciferin-luciferase reaction and a luminometer. A media containing luterial showed an increase in ATP concentration compared to a media without luterial, indicating that luterial has the ability to produce ATP. SSH and SSF were further added to the media and their effects on ATP production by luterial were examined. A media containing SSF induced higher ATP production by luterial compared to a media with SSH, thus finding a medium mix that is capable of efficiently increasing the ATP production by luterial (FIG. 18).

(5) Content of Nucleic Acids

It was found by DAPI and acridine orange (AO) staining that luterial contains not only RNA, but also DNA. Specifically, AO is known to stain RNA with orange AO at an excitation wavelength of 460 nm and an emission wavelength of 650 nm, and DNA with green at an excitation wavelength of 502 nm and an emission wavelength of 525 nm. DAPI is known to positively stain for DNA. Luterial according to the present invention was confirmed to contain RNA and DNA using the staining test as described above (FIGS. 5 and 6). RNA in luterial were further isolated and purified using an extraction kit, and then subjected to agarose gel electrophoresis after qRT-PCR against human GAPDH gene transcripts. It was found that the expression level of human GAPDH gene changed depending on the size of the luterial (FIGS. 2(h), 16 and 17).

(6) 16S rRNA Sequencing

The gDNA of luterial was extracted using a FastDNA SPIN Kit (MP Biomedicals, Cat 6560-200), and then the 16S rRNA gene was amplified using the primers shown in Tables 1 and 2 below.

Figure 24A:
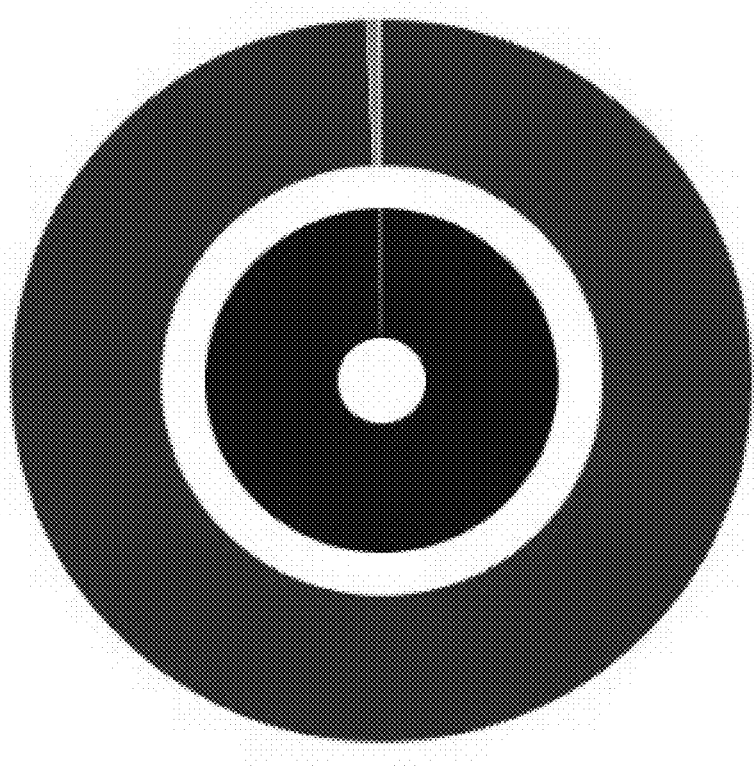
FIG. 24 shows percentage of bacterial homology of luterial DNA as determined by 16S rRNA sequencing of luterials having various sizes, derived from the blood of healthy persons (blood pH: 7.2-7.4) ((a): 100 nm or less; (b): 100-200 nm; (c): 200-400 nm; (d): 400-800 nm).
Figure 24B:
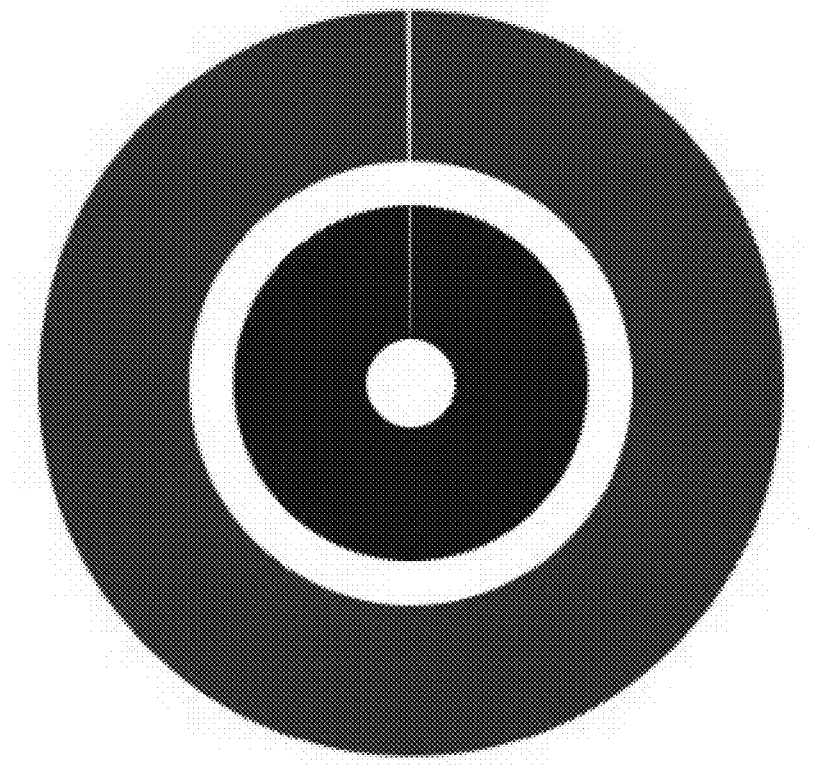
Figure 24D:
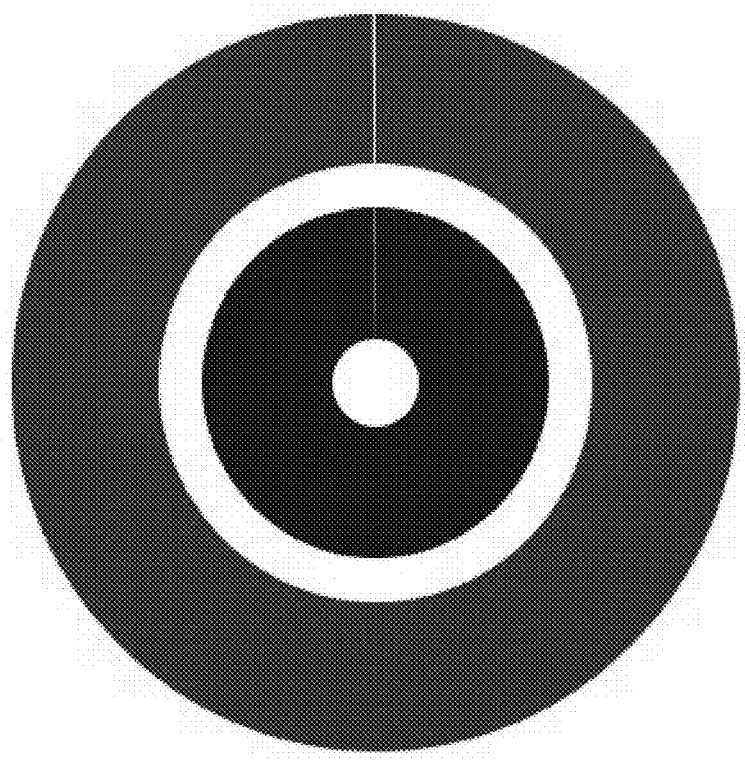

In addition, the 1461 amplified gene fragments were analyzed for their homology using GenBank database (NCBI database). As a result, luterials derived from blood and sperm showed 16S rRNA sequences having homology with those of genes derived from β-proteobacteria, γ-proteobacteria, Acidobacteria, Cyanobacteria, Actinobacteria, Firmicutes and eukaryotes, and showed integrative characteristics corresponding to those of an intermediary between a prokaryote and an eukaryote (FIGS. 24 and 25).

It was observed that, in an optimal condition (blood pH: 7.2-7.4), blood-derived luterial showed homology with genes derived from β-proteobacteria and γ-proteobacteria (FIG. 24) and had a size of 50-800 nm.

In normal conditions, sperm-derived luterial showed homology with genes derived from β-Proteobacteria and γ-Proteobacteria, Bacteroidetes and Chordata.

On the contrary, in an acidic condition, not only genes derived from β-proteobacteria and γ-proteobacteria as in normal conditions, but also other diverse bacteria-derived genes and eukaryote-derived genes were expressed. The luterial mainly expressed the 16S rRNA characteristics of Streptophyta and planctomy (FIG. 25) and grew to a size of 400-2000 nm.

TABLE 1

| | | Forward primers | |
|---|---|---|---|
| Taxon | Name | Sequence (Adaptor-key-linker-target sequence) | SEQ ID NOs: |
| Bacteria | B16S-F | 5'-CCTATCCCCTGTGTGCCTTG GCAGTC-TCAG-AC-GAGTTTGA TCMTGGCTCAG-3' | 1 |
| Bifido-bacterium | Bif16S-F | 5'-CCTATCCCCTGTGTGCCTTG GCAGTC-TCAG-AC-GGGTTCGA TTCTGGCTCAG-3' | 2 |

TABLE 2

| Taxon | Name | Reverse primers Sequence (Adaptor-key-linker-target sequence) | SEQ ID NO: |
|---|---|---|---|
| Bacteria | B16-7-4 | 5'-CCATCTCATCCCTGCGTGTCTCCGAC-TCAG-AGAGCTG-AC-WTTACCGCGGCTGCTGG-3' | 3 |
| Bacteria | B16-7-7 | 5'-CCATCTCATCCCTGCGTGTCTCCGAC-TCAG-TCAGATG-AC-WTTACCGCGGCTGCTGG-3' | 4 |
| Bacteria | B16-7-8 | 5'-CCATCTCATCCCTGCGTGTCTCCGAC-TCAG-CGATGAG-AC-WTTACCGCGGCTGCTGG-3' | 5 |
| Bacteria | B16-7-12 | 5'-CCATCTCATCCCTGCGTGTCTCCGAC-TCAG-TCTGCAG-AC-WTTACCGCGGCTGCTGG-3' | 6 |
| Bacteria | B16-7-13 | 5'-CCATCTCATCCCTGCGTGTCTCCGAC-TCAG-AGCGATG-AC-WTTACCGCGGCTGCTGG-3' | 7 |
| Bacteria | B16-8-3 | 5'-CCATCTCATCCCTGCGTGTCTCCGAC-TCAG-ATGCTGAG-AC-WTTACCGCGGCTGCTGG-3' | 8 |
| Bacteria | B16-8-4 | 5'-CCATCTCATCCCTGCGTGTCTCCGAC-TCAG-TACAGCAG-AC-WTTACCGCGGCTGCTGG-3' | 9 |
| Bacteria | B16-8-18 | 5'-CCATCTCATCCCTGCGTGTCTCCGAC-TCAG-ATCGTGTG-AC-WTTACCGCGGCTGCTGG-3' | 10 |
| Bacteria | B16-8-21 | 5'-CCATCTCATCCCTGCGTGTCTCCGAC-TCAG-CTACACAG-AC-WTTACCGCGGCTGCTGG-3' | 11 |
| Bacteria | B16-9-4 | 5'-CCATCTCATCCCTGCGTGTCTCCGAC-TCAG-CGTGTACTG-AC-WTTACCGCGGCTGCTGG-3' | 12 |
| Bacteria | B16-9-5 | 5'-CCATCTCATCCCTGCGTGTCTCCGAC-TCAG-CTGTCTACG-AC-WTTACCGCGGCTGCTGG-3' | 13 |
| Bacteria | B16-9-8 | 5'-CCATCTCATCCCTGCGTGTCTCCGAC-TCAG-AGTCACTAG-AC-WTTACCGCGGCTGCTGG-3' | 14 |
| Bacteria | B16-9-12 | 5'-CCATCTCATCCCTGCGTGTCTCCGAC-TCAG-AGCTCACTG-AC-WTTACCGCGGCTGCTGG-3' | 15 |
| Bacteria | B16-10-6 | 5'-CCATCTCATCCCTGCGTGTCTCCGAC-TCAG-ATCACGTGCG-AC-WTTACCGCGGCTGCTGG-3' | 16 |
| Bacteria | B16-10-7 | 5'-CCATCTCATCCCTGCGTGTCTCCGAC-TCAG-ATAGCTCTCG-AC-WTTACCGCGGCTGCTGG-3' | 17 |
| Bacteria | B16-10-8 | 5'-CCATCTCATCCCTGCGTGTCTCCGAC-TCAG-AGTGAGCTCG-AC-WTTACCGCGGCTGCTGG-3' | 18 |
| Bacteria | B16-10-9 | 5'-CCATCTCATCCCTGCGTGTCTCCGAC-TCAG-AGTCTGACTG-AC-WTTACCGCGGCTGCTGG-3' | 19 |
| Bacteria | B16-11-1 | 5'-CCATCTCATCCCTGCGTGTCTCCGAC-TCAG-TCATATACGCG-AC-WTTACCGCGGCTGCTGG-3' | 20 |
| Bacteria | B16-11-2 | 5'-CCATCTCATCCCTGCGTGTCTCCGAC-TCAG-TAGATAGTGCG-AC-WTTACCGCGGCTGCTGG-3' | 21 |
| Bacteria | B16-11-3 | 5'-CCATCTCATCCCTGCGTGTCTCCGAC-TCAG-ACGTCTCTACG-AC-WTTACCGCGGCTGCTGG-3' | 22 |
| Bacteria | B16-11-4 | 5'-CCATCTCATCCCTGCGTGTCTCCGAC-TCAG-CTAGAGACACT-AC-WTTACCGCGGCTGCTGG-3' | 23 |

(7) Differences from Exosomes and Mitochondria

Table 3 below summarizes the differences of luterials from exosomes and mitochondria.

TABLE 3

| No. | Category | Exosomes | Luterials | Mitochondria |
|---|---|---|---|---|
| 1 | Size | 20~120 nm | 50~800 nm | 400~1,000 nm |
| 2 | Fluorescence | (CD63antibody)GFP+ | (CD63antibody)GFP− | (CD63antibody)GFP− |
| 3 | | Mitotracker Red− | Mitotracker Red+ | Mitotracker Red+ |
| 4 | | Janus Green B− | Janus Green B+ | Janus Green B+ |
| 5 | | Rhodamine 123− | Rhodamine 123+ | Rhodamine 123+ |
| 6 | Mobility | − | 13~25 μm/sec | − |
| 7 | Growth in Culture | − | + | − |
| 8 | Natural Growth | − | + | − |
| 9 | ATP Synthesis | − | + | + |
| 10 | Auto-fluorescence | − | + | N/A |
| 11 | Fusion | + | + | + |
| 12 | Kiss-and-run (Fission and Fusion) | − | + | + |
| 13 | Sequencing | 18SrRNA 28S rRNA | 16SrRNA (GammaProtebacteria Beta Proteobacteria Bacteroidetes | 16srRNA Alpha Proteobacteria |
| 14 | Habitat | Out of cell | In-and-out of Cell | In cell |

Figure 19:
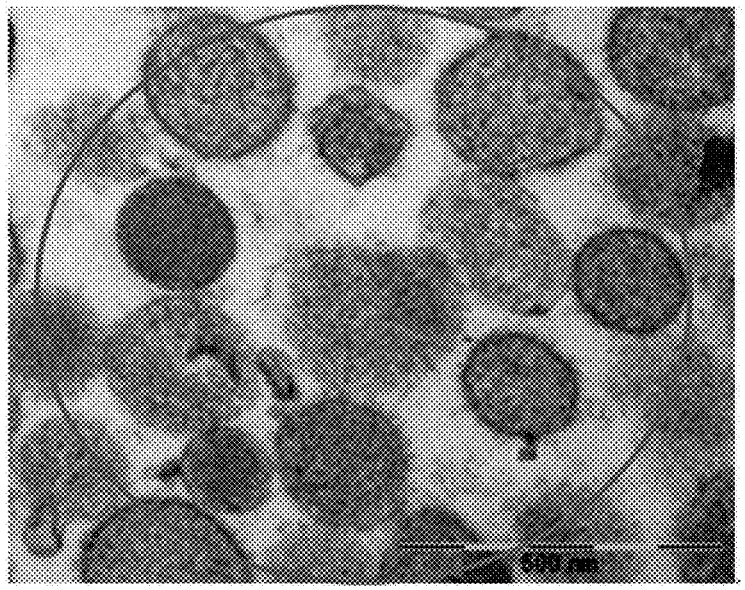
FIG. 19 is a photograph showing a difference between luterial and exosome.
Figure 20:
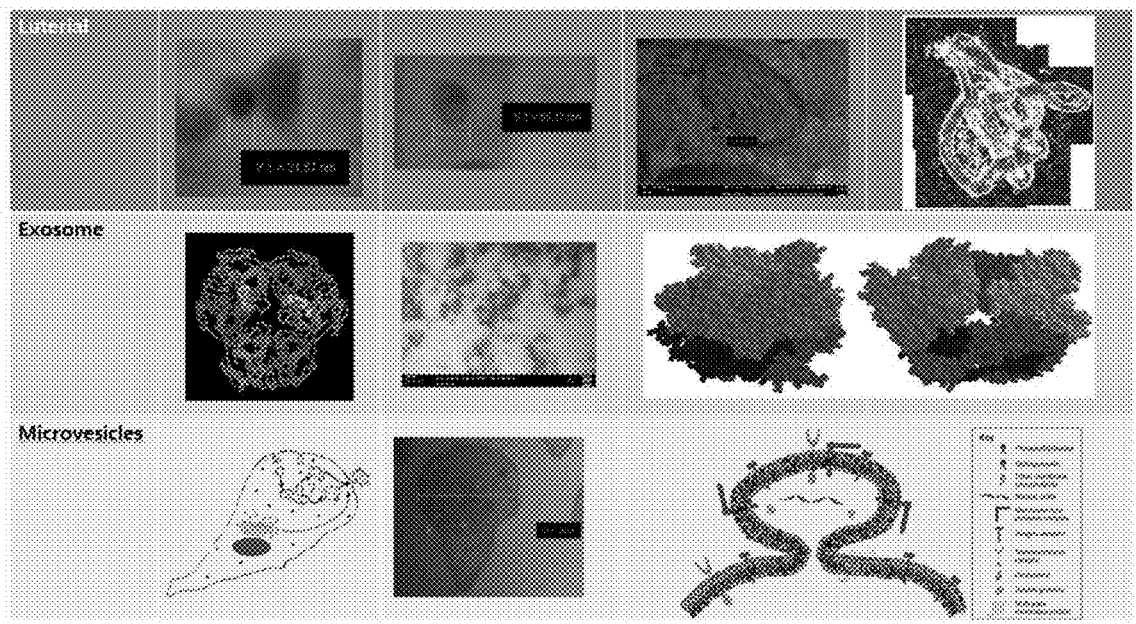
FIG. 20 depicts photographs comparing the morphology between luterial, exosome and microvesicle.

Luterials have an average size of 200-800 nm, which is smaller than that of mitochondria (400-1,000 nm) and greater than that of exosomes (20-120 nm), and exosomes have unclear membranes and a relatively light internal color, whereas luterials have distinct membranes or a packed internal structure (FIG. 19). In addition, luterials have a morphology completely different from those of exosomes and microvesicles (FIG. 20).

In fluorescent staining, luterials unlike exosomes show a reaction similar to that of mitochondria. Luterials are present inside and outside of cells while exosomes are present outside of cells only. Luterials can be supplied by taking foods, whereas mitochondria are intracellular substances that cannot be provided by intake of foods.

In addition unlike exosomes and mitochondria, luterials are mobile, and can grow naturally, the growth thereof can be maintained by culture, and show autofluorescence. Furthermore, luterials, exosomes and mitochondria all undergo fusion events, but in exosomes, kiss-and-run motion and ATP production are absent. Moreover, exosomes are present outside the cells and mitochondria are present inside the cells, whereas luterials can be present inside or outside the cells (FIG. 11).

The results of 16S rRNA sequencing indicated that mitochondria showed homology with α-proteobacteria, whereas luterials showed homology with γ-proteobacteria, β-proteobacteria, Bacteroidetes, Firmicutes and eukaryotes.

In another aspect, the present invention is focused on the body fluid-derived luterial having one or more of the following characteristics:

(a) it shows a positive staining with Janus green B, Acridine Orange and Rhodamine 123 in a fluorescence test;

(b) in an optimal environment (pH 7.2-7.4), it expresses genes homologous to beta-proteobacteria and gamma-proteobacteria, and has a size of 30-800 nm;

(c) in an acidic environment, it expresses genes homologous to not only beta-proteobacteria and gamma-proteobacteria, but also eukaryote Streptophyta, and grows to a size of 400 nm-2000 nm or more;

(d) it is involved in ATP production in normal conditions;

(e) it is a cell or cell-like structure completely different from mitochondria or exosomes;

(f) it is circular or oval in shape in a normal condition, and patient-derived luterial has a size (long axis diameter: 800 nm or more) greater than that of normal luterial and is mutated to form mutant luterial having a non-uniform morphology;

(g) it has a multiple ring-like membrane structure and is adherent;

(h) it can be present inside or outside cells;

(i) it is mobile and undergoes fusion and/or fission events;

(j) mutant luterial bursts in a certain condition and has stemness after bursting; and (k) it has a function of regulating p53 gene and telomeres.

Meanwhile, the size (diameter), area, morphology and nano-tracking speed of luterial differ depending on the presence or absence of disease in an individual, and thus one or more of the above-described characteristics make it possible to diagnose disease or predict disease prognosis. This can be seen from the fact that luterial derived from a healthy person having no disease and luterial derived from a person having disease have different sizes, morphologies, nano tracking speeds, etc.

Figure 10A:
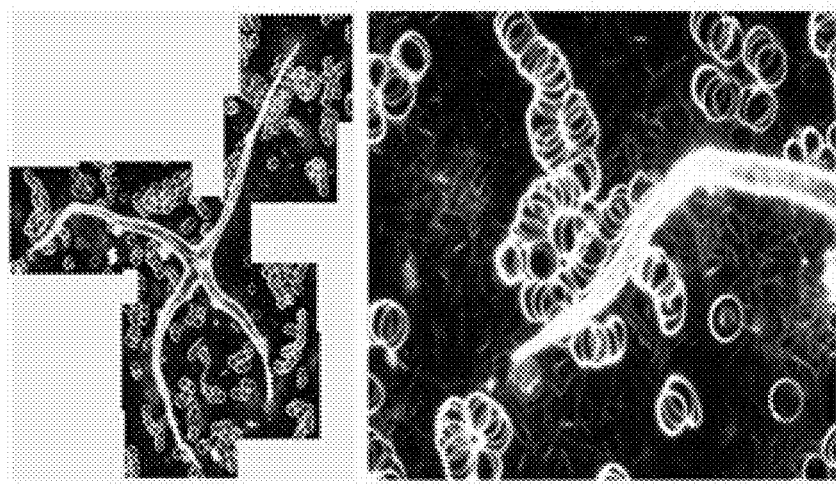
FIG. 10(a) shows cancer patient-derived luterial while forming elongated branches.
Figure 10A:
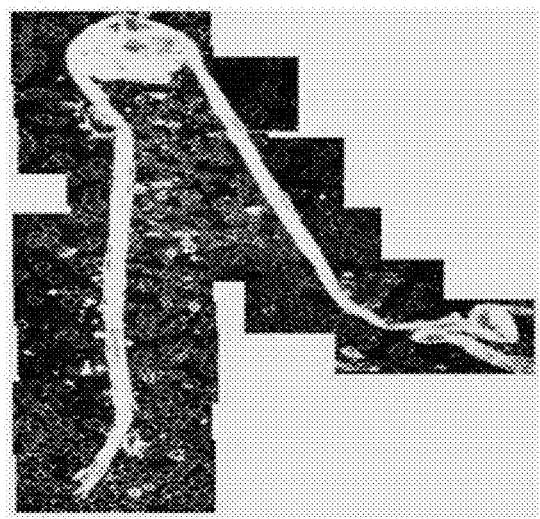
Figure 10B:
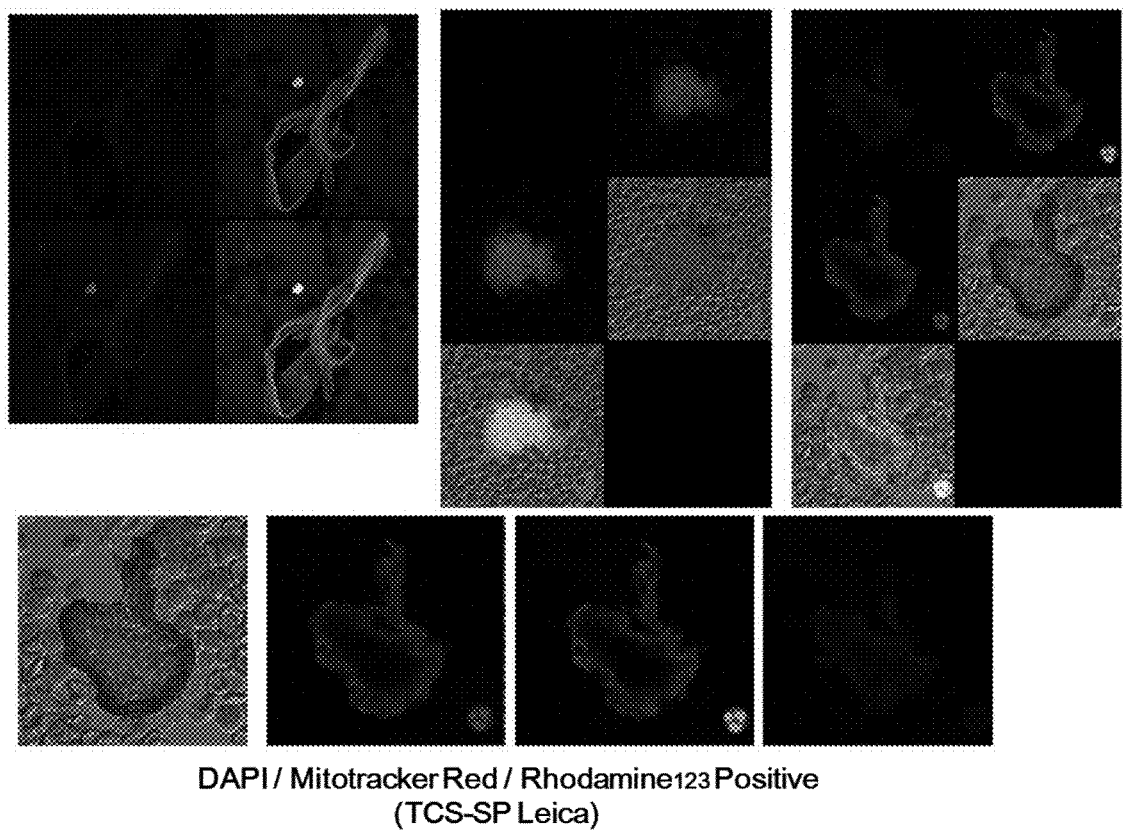
FIG. 10(b) shows cancer patient-derived luterial stained with DAPI (4',6-diamidino-2-phenylindole), Mito-tracker and Rhodamine 123.

Normal luterials in healthy persons merely form double spores undergoing fission, but luterials (mutant luterials) in patients with chronic disease or cancer have characteristics in that they fuse or coagulate with one another or burst to adhere to cells such as erythrocytes or cancer cells, thereby changing their morphology and size abnormally (FIGS. 8 to 10). Mutant luterials are highly adherent, and thus the fusion thereof is accelerated by the above-described cycle to increase their size to about 600-800 nm or more, and any of such mutant luterials may also have a size of 200 μm (200,000 nm) or more. The present inventors found that the morphology of luterials is consistent depending on the kind or progress of cancer, and the content of this finding was filed for a patent (Korean Patent Application No. 10-2013-0082060).

Thus, it is possible to diagnose disease or predict disease prognosis by observing the morphological or biochemical characteristics of luterials, indicating that luterials can be used in unlimited applications.

Luterials have a normal form, a flagellum form, a mass form, a rod form, or a combination form. Herein, the normal form may be a form that does not undergo additional modification such as fusion or bursting, with a long axis diameter-to-short axis diameter ratio of 1:1-3:1. The luterials can show a shape close to a circular shape. They appear as small spots in microscopic observation.

The flagellum form may be a form that results from the modification or fusion of luterials to have flagella-like structure attached outside. The present inventors found that the percentage of the flagellum form dramatically increased as cancer progresses to terminal cancer and that this flagellum form luterials were observed in 99.1% of the patients diagnosed as stage 4 cancer (Korean Patent Application No. 2013-0082060). If the percentage of the flagellum-form luterial reaches 80-100%, it would work as a tumor marker to indicate a terminal stage cancer. The survival period of such patients is about 1-4 months, and particularly, patients dominated with flagellum form luterials cannot survive for a long period.

The mass form (M shape) is a form that was changed from the normal form due to the bursting or fusion of luterials. It is an irregular bulky shape whose long axis diameter-to-short axis diameter ratio is not great. Preferably, it may have a long axis diameter-to-short axis diameter ratio of 3:1-5:1. Various forms of the mass form are observed.

The rod form (R shape) refers to a form resulting from the bursting, modification or fusion of luterials. It has a long axis diameter-to-short axis diameter ratio greater than that of the mass shape. Preferably, it may have a long axis diameter-to-short axis diameter ratio of 5:1-12:1. It includes a rod 1 form consisted of circular or oval single chains; and a rod 2 form consisted of two or more single chains bonded to one or another. The rod 1 form refers to the single luterial that has grown to a rod shape. It may result from the bursting and/or mutation. The rod 2 form refers to a rod shaped luterial formed from fusion of two or more luterials. It may result from one or more of bursting, mutation and fusion. The flagellum form may be included in a broad sense in the scope of the rod form, but it would be different from the rod form in that it has a flagellum-like structure. Thus, luterial form should be first determined whether it is of the rod form and then depending on the presence of the flagellum-like structure it should be further categorized into the flagellum form.

The combination form may be a combination of the rod shape and the mass shape. It may mean that a portion of a single micro particulate matter has the rod shape and the other portion thereof has the mass shape.

The rod form may be one selected from the group consisting of: a rod 1 form consisted of a single circular or oval shape; and a rod 2 form consisted of two or more single chains bonded to one another. The combination form may be a combination of the rod shape and the mass shape.

As described above, the morphology of luterials in vivo changes depending on the development and progress of disease, and thus it is possible to diagnose disease or predict disease prognosis by observing the morphological characteristics of luterials. In addition, the morphological change of luterials is also associated with changes in the content of nucleic acids in the luterials and the sequence of the luterials, and thus enabling diagnosis of disease from nucleic acid expression pattern analysis (16S rRNA sequencing) of luterials. For example, it is possible to diagnose disease (particularly cancer) by comparing the 16S rRNA sequence of normal luterial with that of patient-derived luterial. Particularly, co-expression of Streptopyta gene and eukaryote gene can be used as a marker for diagnosing and predicting carcinogenesis.

However, luterials isolated from body fluids discharged from patients or normal people are difficult to observe because they tend to disappear in vitro within a short time or change their shape. In addition, in an abnormal environment, normal luterials are changed into mutant luterials within 24 hours, making it difficult to accurately diagnose or treat diseases. However, according to the culture method of the present invention, luterials can be cultured such that the their size do not exceed certain size (500 nm).

Therefore, in another aspect, the present invention is directed to a method for culturing luterial, comprising: adding water to luterial; and culturing the luterial at a temperature of 18 to 30° C. (preferably 20 to 25° C.) under irradiation with IR light.

The water that is added in the culture process may be saline or PBS solution, but is not limited thereto. The body fluid-derived luterial before culture may be obtained according to the isolation method of the present invention and may have a size of 50-200 nm. The luterial cultured according to the culture method of the present invention may have a size of 300-800 nm. Herein, the luterial can be controlled to a size of 500 nm or less under microscopic observation. After completion of the culture, the luterial may be sorted according to size, and cooled and stored at −80° C. or stored under nitrogen or may also be stored at a temperature above zero. For storage, a preservative may be added to the luterial.

The luterial cultured as described above can be stored for a certain period of time without changing the characteristics of the luterial, and can be effectively used to diagnose disease and predict disease prognosis. As used herein, the expression "without changing the characteristics of luterial" means that the morphology or size of luterial is maintained at a level similar to that before culture in media. In addition, it means that the activity of luterial, such as mobility (e.g., nano-tracking speed), is maintained at a value similar to that before culture.

Specifically, luterial cultured according to the culture method of the present invention may be used for the following purposes. Mutant luterials have an abnormally increased morphology or size due to fusion or coagulation, unlike normal luterials (FIGS. 8 to 10). By culturing the mutant luterials, a substance capable of inhibiting or preventing the mutation of luterials can be screened from the candidate substances by observing whether the changes in cultured luterial mutants.

Furthermore, a substance that promotes the fission of mutant luterials can be screened by treating cultured mutant luterials with a candidate substance or means. Since mutant luterials show patterns of fusion or coagulation events (FIGS. 8, 9 and 11), by treating the mutant luterials with a candidate substance and examining whether it promotes the fission of mutant luterials to have the size of normal luterials, it would be possible to screen for a substance that inhibits the mutation of luterials or converts mutant luterials to normal luterials, that is, a substance that prevents disease caused from mutant luterials.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Figure 21:
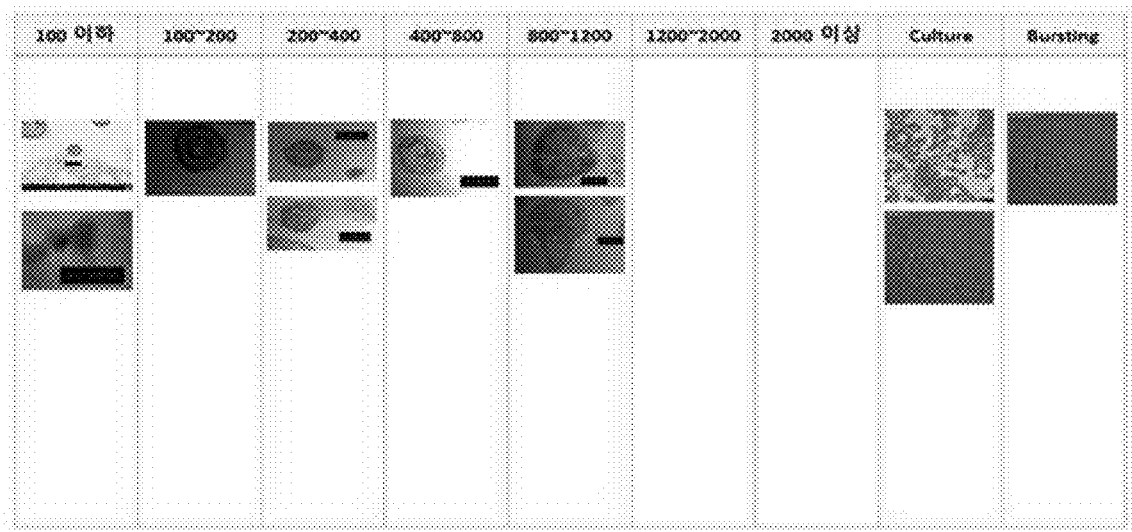
FIG. 21 depicts transmission electron microscope (TEM) images of a luterial library described in an example of the present invention.

Example 1: Isolation of Blood-Derived Luterials 50 cc of blood was collected from a non-small cell lung cancer patient and passed through a filter having a pore size of 0.8 μm or more, and unfiltered substances were removed. The filtered blood was repeatedly centrifuged at 120,000-500,000 g for 5-10 minutes to remove general microvesicles such as exosomes collected in pellets, and the supernatant was collected. The supernatant was irradiated with visible light, and the gathered luterial particles with mobility were isolated by pipetting. Because luterial is autofluorescent and mobile, luterial particles could be visualized by irradiation with visible light as described above. At this time, mobile luterial particles were isolated by pipetting under observation with a dark-field microscope or a confocal microscope. The isolated luterials were filtered through a filter having a pore size of 50 nm, and only an unfiltered portion was washed with PBS, thereby obtaining luterials. According to the above procedures, luterials having a long axis diameter of 50-800 nm could be obtained, which could be observed through a dark-field microscope or a confocal microscope. The obtained luterials were sorted according to size into 50-200 nm (developmental phase)/200-400 nm (maturation phase)/400-600 nm (mitosis phase)/600-800 nm (over-mitosis phase). According to a similar method, a library of luterials with various sizes as shown in FIG. 21 was constructed, and the morphologies of luterials with various sizes are shown in FIG. 2.

Example 2: Isolation of Semen-Derived Luterials

Semen was centrifuged at 2000-4000 rpm for 5-30 minutes, and the supernatant was filtered through a filter having a pore size of 2-5 μm. The filtered solution was centrifuged at 3000-7000 rpm for 5-20 minutes, followed by filtration through a filter having a pore size of 0.5-2 μm. Because luterials are autofluorescent and mobile, luterial particles can be visualized when the filtered solution was irradiated with visible light. At this time, mobile luterial particles were isolated by pipetting under observation with a dark-field microscope or a confocal microscope. The isolated luterials were filtered through a filter having a pore size of 50 nm, and only an unfiltered portion was washed with PBS, thereby obtaining luterials which could be observed through a dark-field microscope or a confocal microscope.

Example 3: Characteristics of Luterials (1) Structure

Among the luterials obtained in Example 1, luterials having a size of about 50-400 nm were imaged with a confocal laser scanning microscope (Zeiss), a transmission electron microscope, a scanning electron microscope, an atomic force microscope and a confocal scanner (Leica TCS-SP8). As a result, it was shown that the luterials also had a multiple ring-like layers of membrane structure and a non-completed internal cristae structure, similar to mitochondria, and were observed in the same wavelength range as that for mitochondria. In addition, it could be observed that the luterials were circular or oval in shape (FIGS. 1, 1(e), 2(h), 13 and 14).

(2) Staining Characteristics

Among the luterials obtained in Example 1, luterials having a size of about 50-800 nm were stained with Mito-tracker, Rhodamine 123, Acridine Orange and Janus green B, and tested for their positive staining. The results showed that even the plant-derived luterials were also stained by Mito-tracker, Rhodamine 123, Acridine Orange and Janus green B (FIGS. 2(a), 2(b), 2(f) and 2(j), and FIGS. 3 to 6).

(3) Autofluorescence

Figure 5:
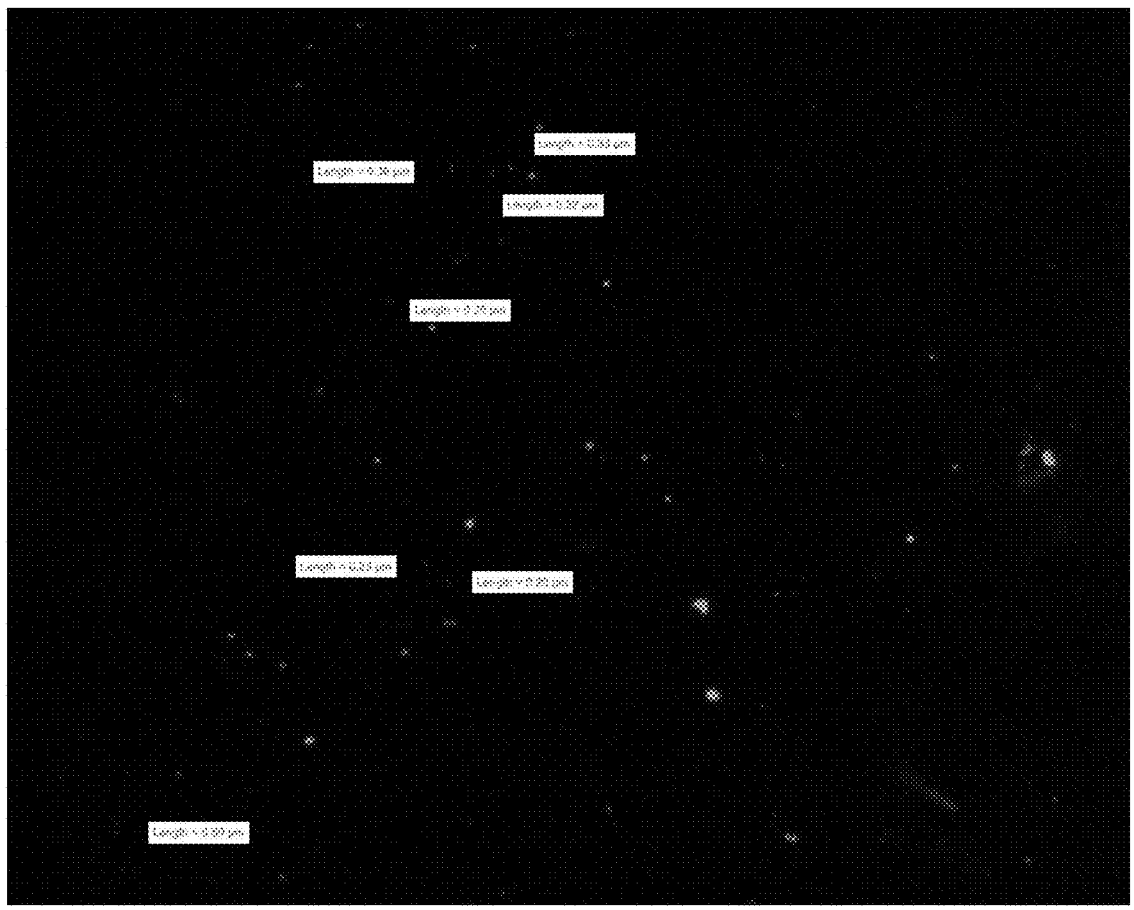
FIG. 5 is an image showing the results of staining luterial with Acridine Orange and then observing whether the luterial would be positively stained.
Figure 6:
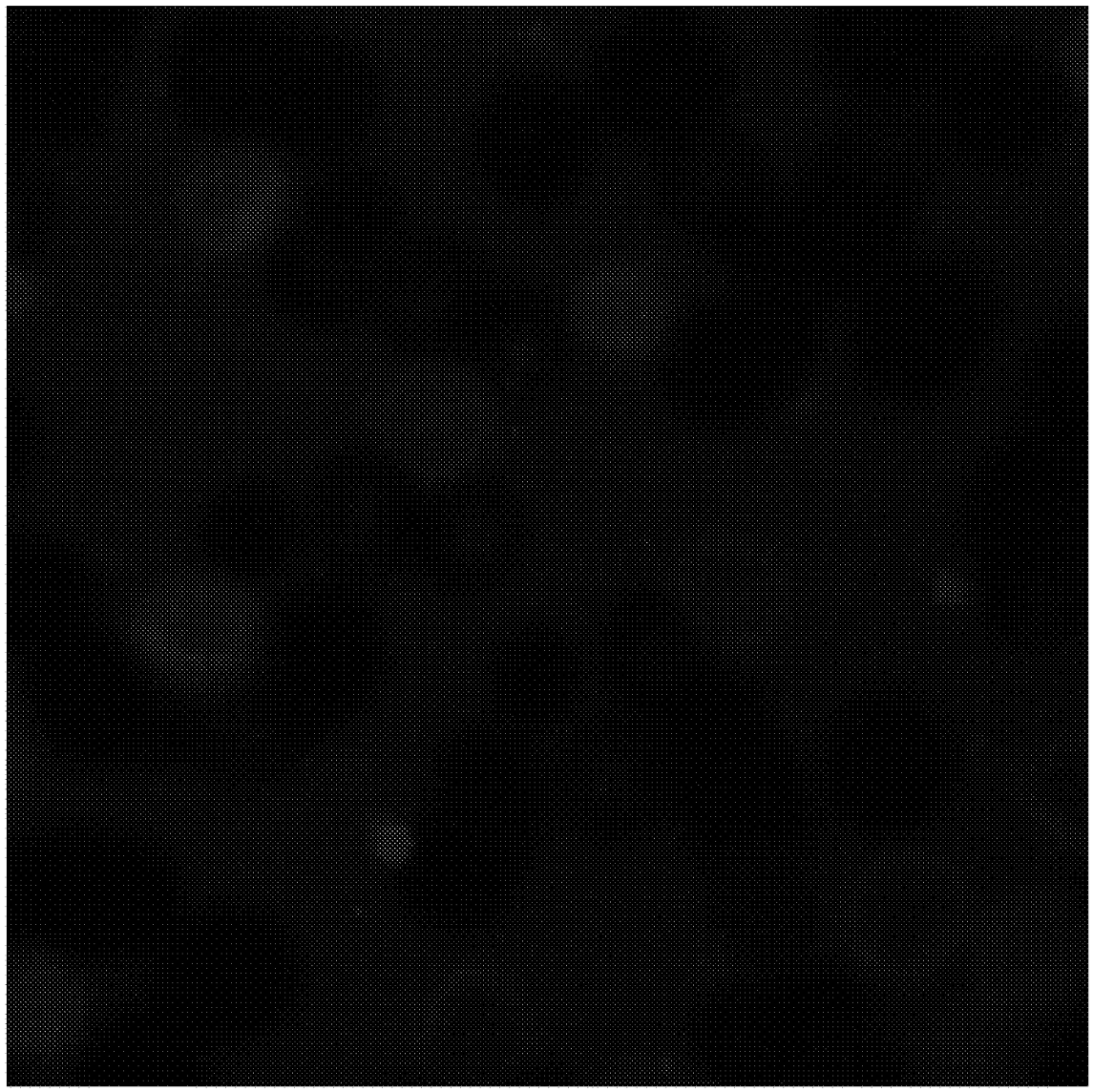
FIG. 6 is an image showing the results of staining luterial with DAPI (4',6-diamidino-2-phenylindole) and then observing whether the luterial would be positively stained.

Among the luterials obtained in Example 1, luterials having a size of about 50-800 nm were analyzed through fluorescence images. The result showed that luterials responded to light (FIG. 5).

(4) Mobility

Figure 7:
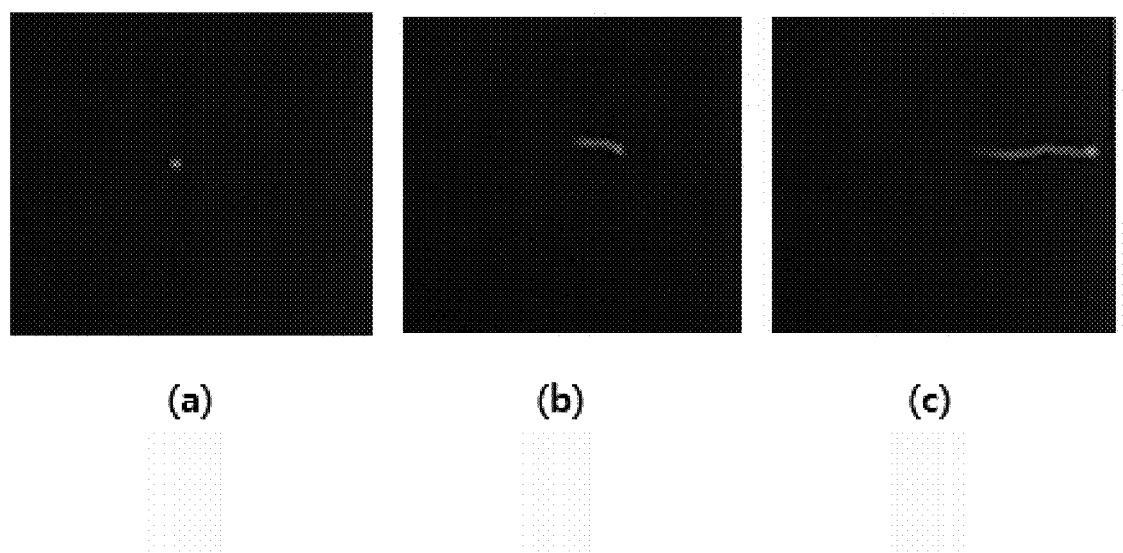
FIG. 7 depicts images showing the results of measuring the mobility of luterial using nano-trackers ((a) before measurement; (b) after 1 second; (c) after 3 seconds).

The mobility of luterials obtained in Example 1 was measured by nano-tracking (3i Inc., USA) analysis. Specifically, luterials were observed with a bright-field microscope, tracking was set in the center of the luterial, and nano-tracking was performed. Then, the real-time movement trajectory of the luterial was recorded and the speed per second of the luterial was calculated (FIG. 7).

As a result, the nano-tracking speed of the luterials according to the present invention was measured to be about 13-25 µm/sec.

(5) Analysis of Whether Luterials Contain RNA and DNA

The luterials having a size of 200-400 nm, isolated in Example 1, were imaged with an atomic force microscope. As shown in FIGS. 2(h), 15, 16 and 17, luterials contain nucleic acids such as RNA or DNA.

In order to isolate total RNA and DNA from luterials having a size of 200-400 nm isolated in Example 1, a QIAGEN kit (RNeasy Micro Kit: Cat 74004) was used, followed by quantification using an Experion RNA (DNA) StdSens (Bio-Rad) chip.

Luterials were recovered by centrifugation (at 8,000 g for 1 hr 30 min), and then lysed by adding 50 µl of lysis buffer RLT plus (guanidine isothiocyanate, detergents) from the kit mixed with 3.5 µl of beta-mercaptoethanol and then passing them 5-10 times through a syringe equipped with a 20-gauge needle. The sample lysis buffer was then transferred to an AllPrep DNA spin column, followed by centrifugation (at ≥8000 g for 15 sec) to separate DNA remaining on the column from the RNA contained in the buffer that passed through the column.

Next, 350 µl of 70% ethanol was added to the same volume of the sample lysis buffer that passed through the column (RNA) and well mixed. Then 700 µl of the mixture was transferred to a RNease MinElute spin column and centrifuged (at ≥8000 g for 15 sec), and the buffer that passed through the column was removed. The column was washed sequentially with 350 µl of RW1, 500 µl of RPE buffer and 500 µl of 80% ethanol. All the centrifugation procedures (≥8000 g for 15 sec) used as described above were performed under the same conditions. To obtain RNA, 14 µl of RNease-free solution was added to the column and then centrifuged (at ≥8000 g for 60 sec), thereby isolating luterial RNA.

For isolation of genomic DNA (gDNA), a FastDNA SPIN Kit (MP Biomedical) was used. The isolated luterials were added to the tube, followed by addition of 978 µl of sodium phosphate buffer and 122 µl of MT buffer. The mixture was homogenized for 40 sec, and then centrifuged at 14,000 g for 10 min to collect the supernatant, after which 250 µl of PPS (Protein Precipitation Solution) was added to the supernatant and mixed for 10 min. After centrifugation at 14,000 g for 5 min, and the supernatant was transferred into a 15 ml tube, and this procedure was repeated twice. For DNA binding, the resulting supernatant was placed on a rotor for 2 minutes, and then placed on a silica matrix support for 3 minutes. 600 µl of the supernatant was carefully added to a SPIN filter and was centrifuged at 14,000 g for 1 min, and then the supernatant was discarded, and 500 µl of SEWS-M was added to the remaining pellets and resuspended. After centrifugation for 1 min, the supernatant was discarded, and centrifugation was repeated such that any buffer would not remain. Then, 50 µl of DES (DNase/Pyrogen-Free Water) was added to the remaining material, followed by centrifugation at 14,000 g for 1 min, and then genomic DNA was isolated.

Figure 16A:
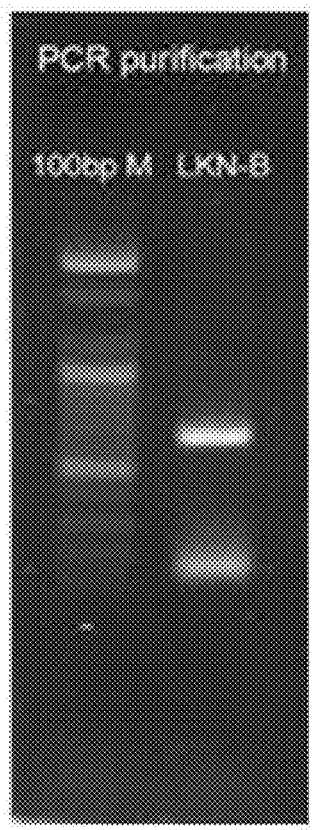
FIG. 16(a) shows the bioanalyzer results of analyzing whether luterial contains DNA.
Figure 16B:
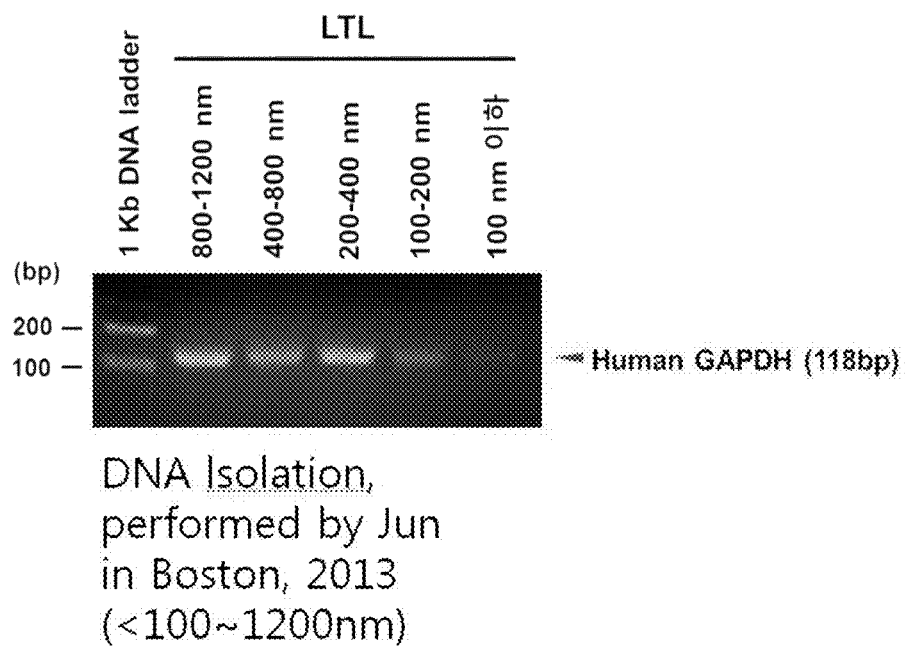
FIG. 16(b) shows the results of qRT-PCR, which indicate that the GAPDH gene expression of DNA changes depending on the size of luterial.
Figure 17:
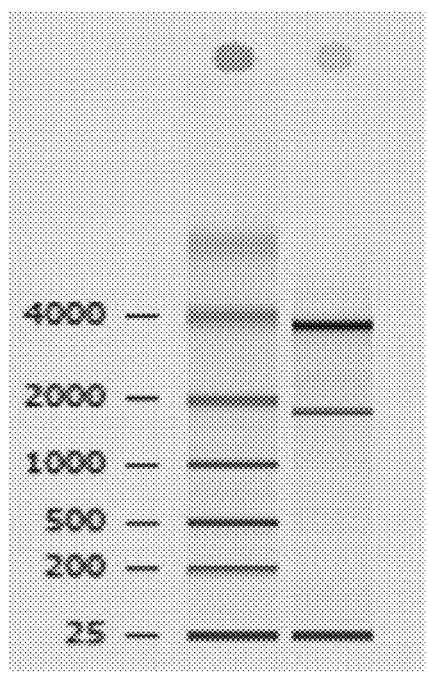
FIG. 17 shows the bioanalyzer results of analyzing whether luterial contains DNA.

Quantification was performed using an Experion RNA (DNA) StdSens (Bio-Rad) chip. The result, as shown in FIGS. 16 and 17, indicated that the luterials contained RNA and DNA.

(6) 16S rRNA Sequencing 16S rRNA (ribosomal ribonucleic acid) is a DNA that interacts with various proteins to form ribosomes. Because the rate of change in the nucleotide sequence of 16S rRNA is significantly lower than those of the nucleotide sequences of most of other genes in the genome, it is recognized that the similarity of the 16S rRNA sequence reflects the phylogenetic distance between organisms.

① Blood-Derived Luterials

The luterials obtained in Example 1 were treated using a FastDNA SPIN kit (MP Biomedicals, Cat 6560-200) to extract gDNA. Using the extracted gDNA, the 16S rRNA of the luterial was amplified using a PCR-premix (iNtRON Biotechnology, Korea) and primers of SEQ ID NOs: 1 to 23.

The amplified PCR products were sequenced using a BigDye Terminator Cycle Sequencing Ready Reaction kit (Applied Biosystems, USA) and an automated DNA analyzer system (PRISM 3730XL DNA analyzer, Applied Biosystems). The amplified PCR products were a total of 1461 fragments. Among them, 1407 fragments showed homology with the proteobacteria-derived gene, 20 fragments showed homology with the Acidobacteria-derived gene, and 11 fragments showed homology with the Actinobacteria-derived gene (Table 4).

The fragments with the analyzed nucleotide sequences were combined using SeqMan software (DNASTAR), thereby obtaining the nucleotide sequence of 16S rRNA.

FIG. 24 shows bacterial homologies of luterial DNA of healthy individual as determined by 16S rRNA sequencing of luterials derived from the blood of healthy persons (blood pH: 7.2-7.4), and shows the results of analysis performed for luterials of various sizes ((a): 100 nm or less, (b): 100-200 nm, (c) 200-400 nm, and (d) 400-800 nm). There was no significant difference among the luterial sizes, and luterials all showed homology with the genes derived from Proteobacteria, Firmicutes and Bacteroidetes.

Figure 25A:
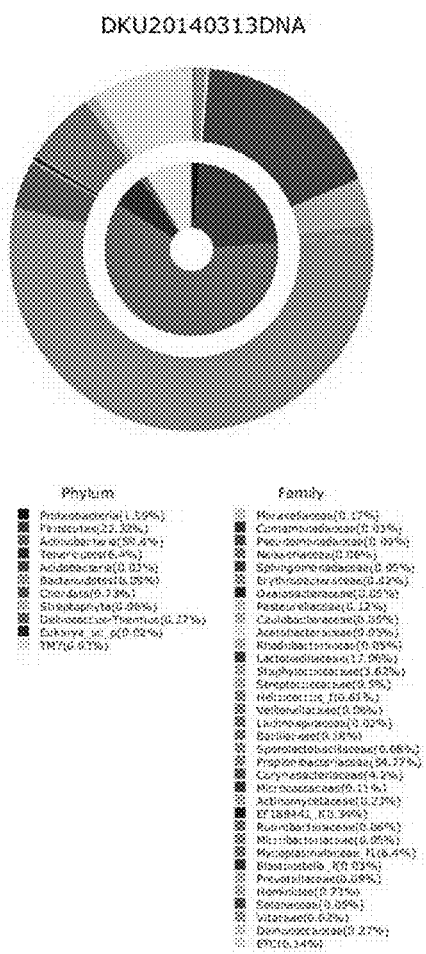
FIG. 25 shows percentage of bacterial homology of luterial DNA as determined by 16S rRNA sequencing of luterials having various sizes, derived from blood and sperm which are in a fatigue and disease status (pH: 7.0 or less) ((a): 100 nm or less; (b): 100-200 nm; (c): 200-400 nm; and (d): 400-800 nm).
Figure 25B:
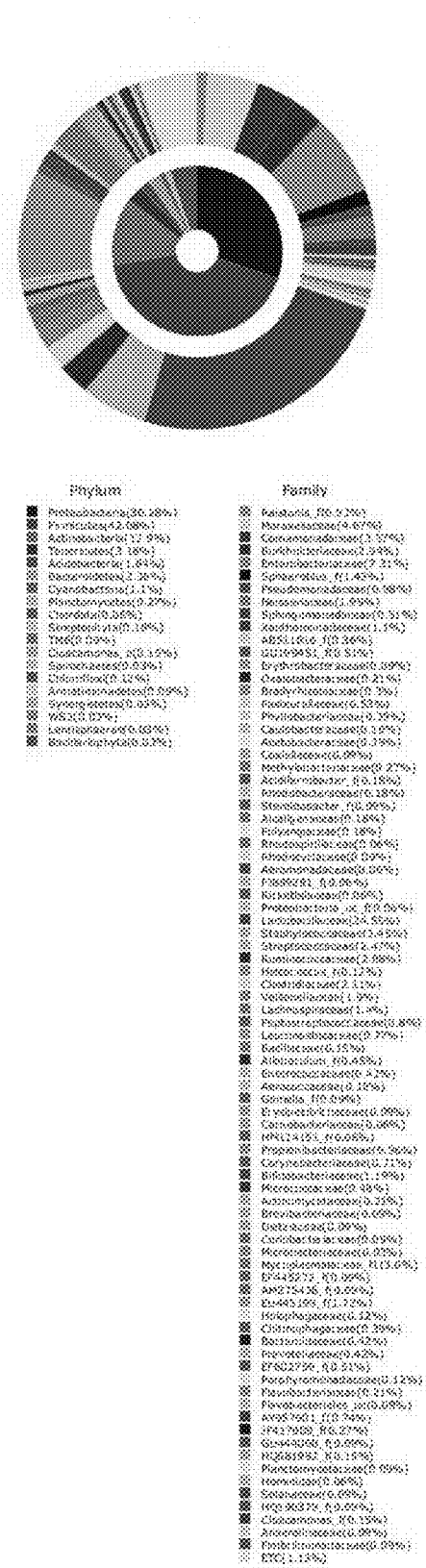
Figure 25C:
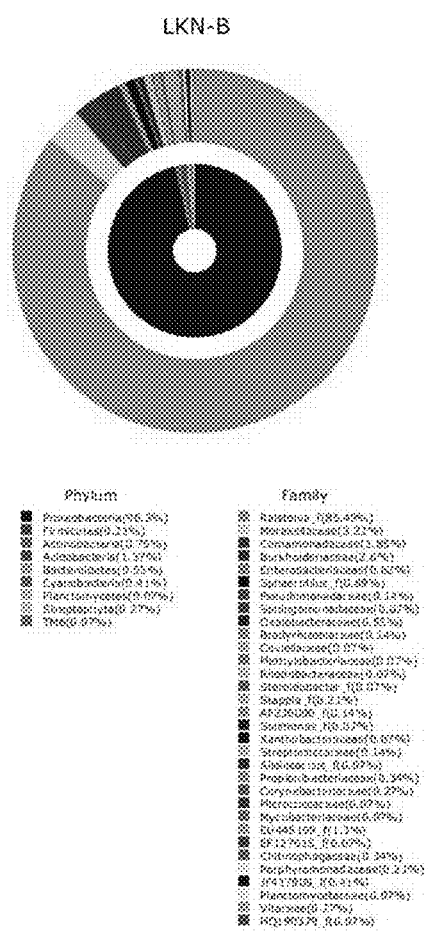
Figure 25D:
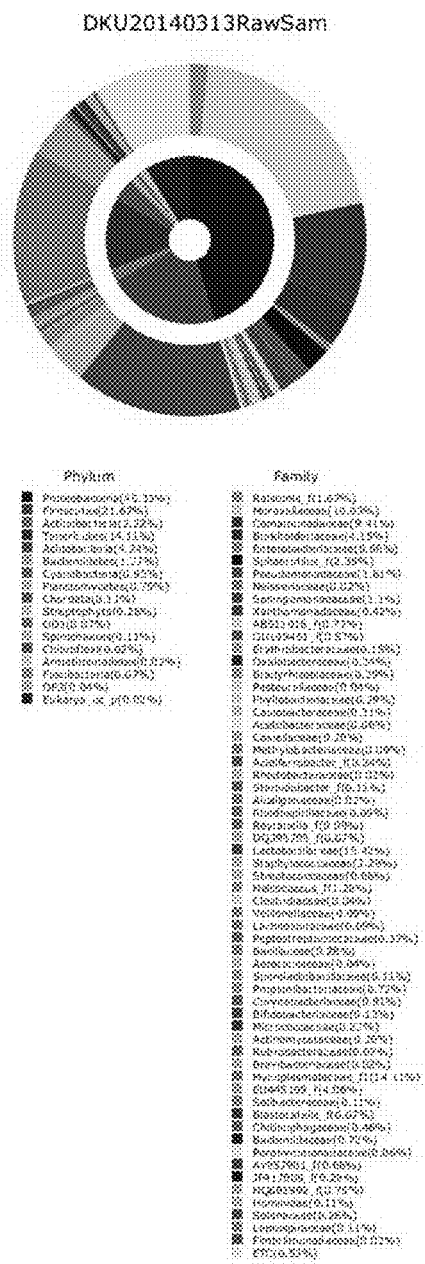

FIG. 25(c) shows bacterial homologies of luterial DNA obtained from the patients with disease. The 16S rRNA sequencing data of 200-400 nm luterials derived from blood of a patient with a fatigue or disease condition (blood pH: 7.0 or less) were used. Unlike in healthy conditions, luterial genes obtained from the patients showed homology with Streptophyta-derived genes.

Figure 26A:
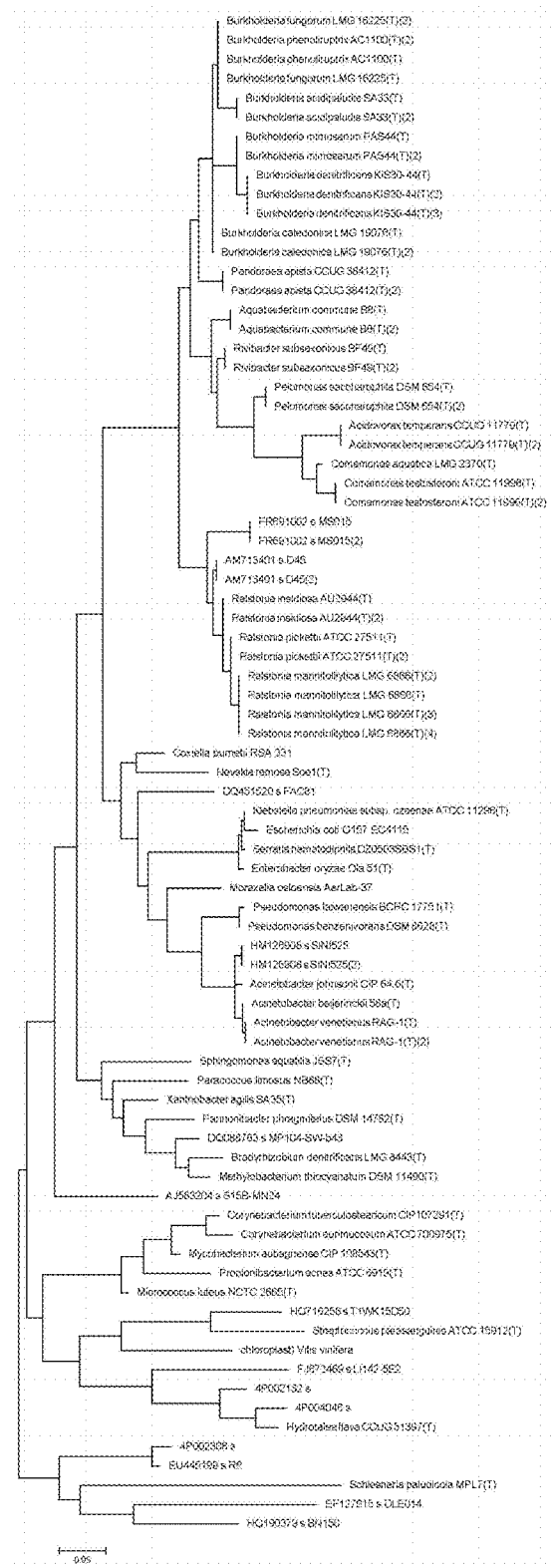
FIGS. 26(a), 26(b) and 26(c) show phylogenetic trees based on the 16S rRNA sequence of blood-derived luterials.
Figure 26B:
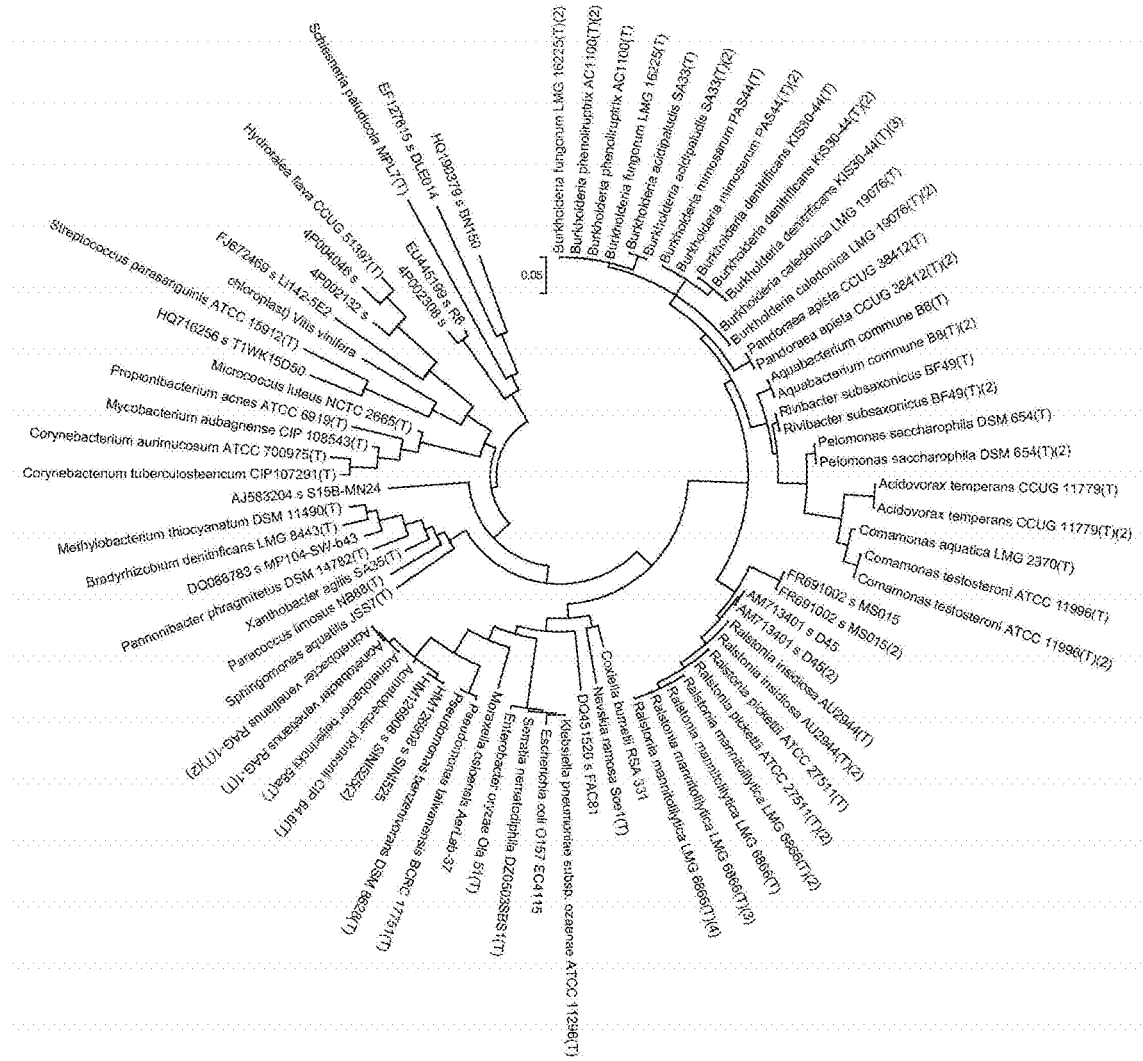
Figure 26C:
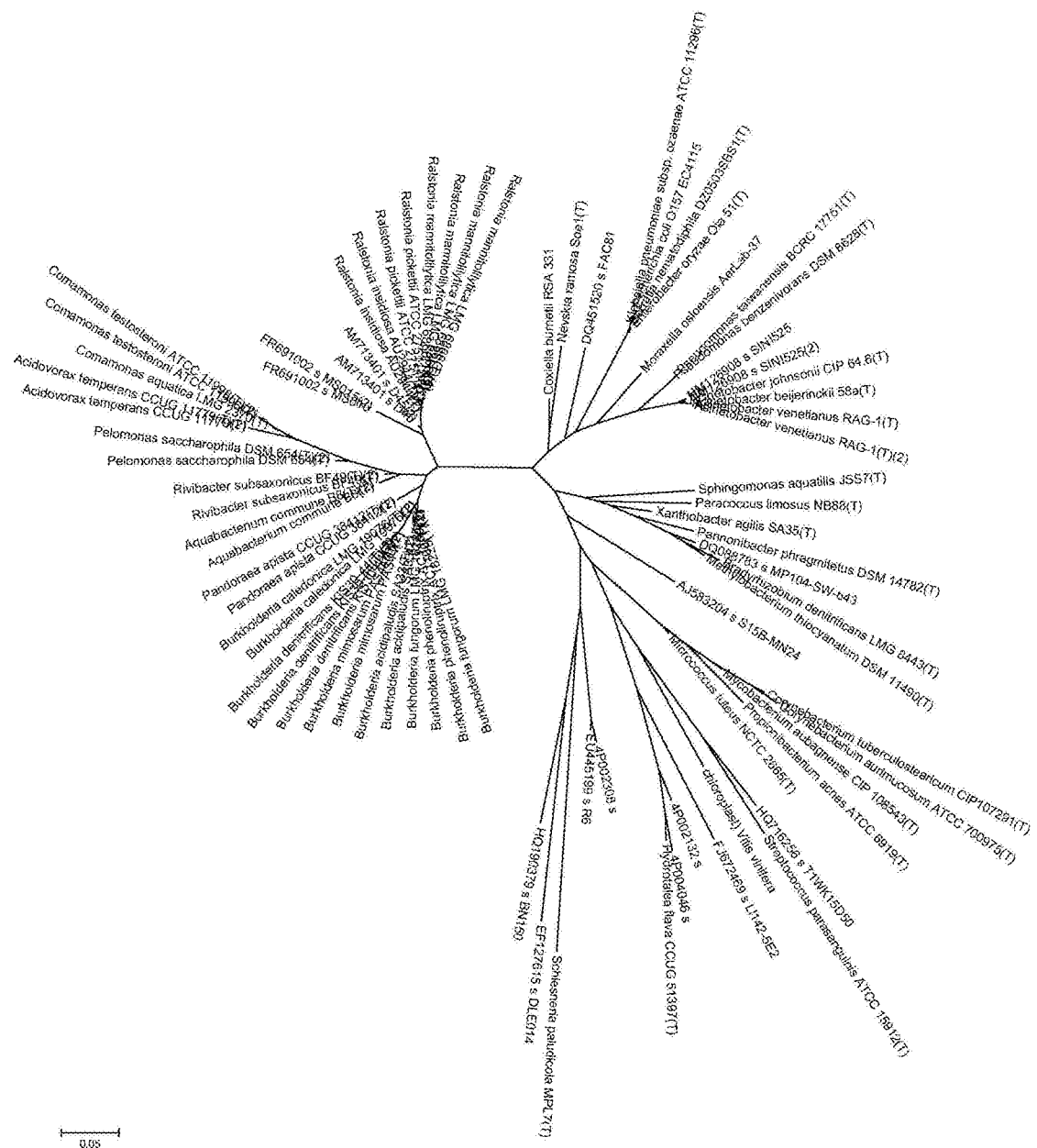

FIGS. 26(a) 26(b) and 26(c) show phylogenetic trees based on the 16S rRNA sequence of blood-derived luterials.

TABLE 4

| Rank | Taxonomy | Name | LKL-B | SUM (Ratio) | LKL-B | Sum (Number) |
|---|---|---|---|---|---|---|
| Phylum | Bacteria;;;Proteobacteria | Proteobacteria | 96.3039 | 96.3039 | 1407 | 1407 |
| Phylum | Bacteria;;;Acidobacteria | Acidobacteria | 1.36893 | 1.36893 | 20 | 20 |
| Phylum | Bacteria;;;Actinobacteria | Actinobacteria | 0.75291 | 0.75291 | 11 | 11 |
| Phylum | Bacteria;;;Bacteroidetes | Bacteroidetes | 0.54757 | 0.54757 | 8 | 8 |
| Phylum | Bacteria;;;Cyanobacteria | Cyanobacteria | 0.41068 | 0.41068 | 6 | 6 |
| Phylum | Eukarya;Viridiplantae;;Streptophyta | Streptophyta | 0.27379 | 0.27379 | 4 | 4 |
| Phylum | Bacteria;;;Firmicutes | Firmicutes | 0.20534 | 0.20534 | 3 | 3 |
| Phylum | Bacteria;;;TM6 | TM6 | 0.06845 | 0.06845 | 1 | 1 |
| Phylum | Bacteria;;;Planctomycetes | Planctomycetes | 0.06845 | 0.06845 | 1 | 1 |

It was shown that the 16S rRNA fragments of the blood-derived luterials showed homology with various bacteria, including beta-proteobacteria, gamma-proteobacteria, Bacteroidetes, Firmicutes and Streptophyta.

Generally, when the relatedness of gDNA in microbial taxonomy is less than 70%, the microorganisms are recognized as independent strains. In addition, it was demonstrated by statistical analysis that, when the homology of the 16S rRNA sequence is less than 97%, the gDNA relatedness is less than 70%. Thus, cells having a homology of 97.0% or more with the 16S rRNA fragments of the luterials were analyzed. As shown in Tables 5 to 7 below, the blood-derived luterials showed a homology of 100% with gamma-proteobacteria, a homology of 97.53% with Firmicutes, and a homology of 97% or more with Bacteroidetes.

Meanwhile, as shown in Table 8, abnormal acidic luterials showed a homology of 99% or more with Streptophyta.

TABLE 5

Characteristics of Luterial by 16S rRNA Seq

| Raw data Seq Name | Sequence | Hit accession | Similarity | Taxonomic assignment |
|---|---|---|---|---|
| IOFBYRO01DTJ3I | ATTGAACGCTGGCGGCAGGCTTAACACA TGCAAGTCGAGCGGAGATGAGGTGCTTG CACCTTATCTTAGCGGCGGACGGTGAGT AATGCTTAGGAATCTGCCTATTAGTGGG GGGACAACATTCCGAAAGGGATGCTAAT ACCGCATACGTCCTACGGGAGAAAGCAG GGGATCTCCGGACCTTGCGCTAATAGAT GAGCCTAAGTCGGATTAGCTAGTTGGTG GGGTAAAGGCCTACCAAGGCGACGATCT GTAGCGGGTCTGAGAGGATGATCCGCCA CACTGGGACTGAGACACGGCCCAGACTC CTACGGGAGGCAGCAGTGGGGAATATTG GACAATGGGGGAACCCTGATCCAGCCA TGCCGCGTGTGTGAAGAAGGCCTTATGG TTGTAAAGCACTTTAAGCGAGGAGGAGG CTACTGAGACTAATACTCTTGGATAGTGG ACGTTACTCGCAGAATAAGCACCGGCTA ACTCTGTG | AM410704 | 100 | Bacteria;;;Proteobacteria;; Gammaproteobacteria;; Pseudomonadales;; Moraxellaceae;; *Acinetobacter*; *Acinetobacter junii*;; LMG 998-AM410704(T) |
| IOFBYRO01DUOG5 | ATTGAACGCTGGCGGCAGGCTTAACACA TGCAAGTCGAGCGGAGATGAGGTGCTTG CACCTTATCTTAGCGGCGGACGGGTGAG TAATGCTTAGGAATCTGCCTATTAGTGGG GGACAACATTCCGAAAGGAATGCTAATA CCGCATACGTCCTACGGGAGAAAGCAGG GGATCTTCGGACCTTGCGCTAATAGATG AGCCTAAGTCGGATTAGCTAGTTGGTGG GGTAAAGGCCTACCAAGGCGACGATCTG TAGCGGGTCTGAGAGGATGATCCGCCAC ACTGGGACTGAGACACGGCCCAGACTCC TACGGGAGGCAGCAGTGGGGAATATTG GACAATGGGGGAACCCTGATCCAGCCA TGCCGCGTGTGTGAAGAAGGCCTTATGG TTGTAAAGCACTTTAAGCGAGGAGGAGG CTACTGAGACTAATACTCTTGGATAGTGG ACGTTACTCGCAGAATAAGCACCGGCTA ACTCTGTG | AM410704 | 100 | Bacteria;;;Proteobacteria;; Gammaproteobacteria;; Pseudomonadales;; Moraxellaceae;; *Acinetobacter*; *Acinetobacter junii*;; LMG 998-AM410704(T) |
| IOFBYRO01BHYT4 | TTGAACGCTGGCGGCAGGCTTAACACAT GCAAGTCGAGCGGAGATGAGGTGCTTG CACCTTATCTTAGCGGCGGACGGGTGAG TAATGCTTAGGAATCTGCCTATTAGTGGG GGACAACATTCCGAAAGGGAATGCTAAT ACCGCATACGTCCTACGGGAGAAAGCA GGGGATCTTCGGACCTTGCGCTAATAGA TGAGCCTAAGTCGGATTAGCTAGTTGGT | AM410704 | 100 | Bacteria;;;Proteobacteria;; Gammaproteobacteria;; Pseudomonadales;; Moraxellaceae;; *Acinetobacter;Acinetobacter junii*;; LMG 998-AM410704(T) |

TABLE 5-continued

Characteristics of Luterial by 16S rRNA Seq

| Raw data Seq Name | Sequence | Hit accession | Similarity | Taxonomic assignment |
|---|---|---|---|---|
| | GGGGTAAAGGCCTACCAAGGCGACGAT CTGTAGCGGGTCTGAGAGGATGATCCGC CACACTGGGACTGAGACACGGCCCAGAC TCCTACGGGAGGCAGCAGCGGGGAATA TTGGACAATGGGGGAACCCTGATCCAG CCATGCCGCGTGTGTGAAGAAGGCCTTA TGGTTGTAAAGCACTTTAAGCGAGGAGG AGGCTACTGAGACTAATACTCTTGGATAG TGGACGTTACTCGCAGAATAAGCACCGG CTAACTCTGTG | | | |
| IOFBYRO01CYAL1 | ATTGAACGCTGGCGGCAGGCTTAACACA TGCAAGTCGAGCGGAGATGAGGTGCTTG CACCTTATCTTAGCGGCGGACGGGTGAG TAATGCTTAGGAATCTGCCTATTAGTGGG GGACAACATTCCGAAAGGAATGCTAATA CCGCATACGTCCTACGGGAGAAAGCAGG GGATCTTCGGACCTTGCGCTAATAGATG AGCCTAAGTCGGATTAGCTAGTTGGTGG GGTAAAGGCCTACCAAGGCGACGATCTG TAGCGGGTCTGAGAGGATGATCCGCCAC ACTGGGACTGAGACACGGCCCAGACTCC TACGGGAGGCAGCAGTGGGGAATATTG GACAATGGGGGAACCCTGATCCAGCC ATGCCGCGTGTGTGAAGAAGGCCTTATG GTTGTAAAGCACTTTAAGCGAGGAGGAG GCTACTGAGACTAATACTCTTGGATAGTG GACGTTACTCGCAGAATAAGCACCGGCT AACTCTGTG | AM410704 | 100 | Bacteria;;;Proteobacteria;; Gammaproteobacteria;; Pseudomonadales;; Moraxellaceae;; *Acinetobacter;Acinetobacter junii;;* LMG 998-AM410704(T) |
| IOFBYRO01DRDH1 | ATTGAACGCTGGCGGCAGGCTTAACACA TGCAAGTCGAGCGGAGATGAGGTGCTTG CACCTTATCTTAGCGGCGGACGGGTGAG TAATGCTTAGGAATCTGCCTATTAGTGGG GGACAACATTCCGAAAGGAATGCTAACA CCGCATACGTCCTACGGGAGAAAGCAGG GGATCTTCGGACCTTGCGCTAATAGATG AGCCTAAGTCGGATTAGCTAGTTGGTGG GGTAAAGGCCTACCAAGGCGACGATCTG TAGCGGGTCTGAGAGGATGATCCGCCAC ACTGGGACTGAGACACGGCCCAGACTCC TACGGGAGGCAGCAGTGGGGAATATTG GACAATGGGGGAACCCTGATCCAGCCA TGCCGCGTGTGTGAAGAAGGCCTTATGG TTGTAAAGCACTTTAAGCGAGGAGGAGG CTACTGAGACTAATACTCTTGGATAGTGG ACGTTACTCGCAGAATAAGCACCGGCTA ACTCTGTG | AM410704 | 100 | Bacteria;;;Proteobacteria;; Gammaproteobacteria;; Pseudomonadales;; Moraxellaceae;; *Acinetobacter;Acinetobacter junii;;* LMG 998-AM410704(T) |
| IOFBYRO01BWKSQ | ATTGAACGCTGGCGGCAGGCTTAACACA TGCAAGTCGAGCGGAGATGAGGTGCTTG CACCTTATCTTAGCGGCGGACGGGTGAG TAATGCTTAGGAATCTGCCTATTAGTGGG GGACAACATTCCGAAAGGAATGCTAATA CCGCATACGTCCTACGGGAGAAAGCAGG GGATCTTCGGACCTTGCGCTAATAGATG AGCCTAAGTCGGATTAGCTAGTTGGTGG GGTAAAGGCCTACCAAGGCGACGATCTG TAGCGGGTCTGAGAGGATGATCCGCCAC ACTGGGACTGAGACACGGCCCAGACTCC TACGGGAGGCAGCAGTGGGGAATATTG GACAATGGGGGAACCCTGATCCAGCCA TGCCGCGTGTGTGAAGAAGGCCTTATGG TTGTAAAGCACTTTAAGCGAGGAGGAGG CTACTGAGACTAATACTCTTGGATAGTGG ACGTTACTCGCAGAATAAGCACCGGCTA ACTCTGTG | AM410704 | 100 | Bacteria;;;Proteobacteria;; Gammaproteobacteria;; Pseudomonadales;; Moraxellaceae;; *Acinetobacter;Acinetobacter junii;;* LMG 998-AM410704(T) |

TABLE 5-continued

Characteristics of Luterial by 16S rRNA Seq

| Raw data Seq Name | Sequence | Hit accession | Similarity | Taxonomic assignment |
|---|---|---|---|---|
| IOFBYRO01BWKSO | ATTGAACGCTGGCGGCAGGCTTAACACA TGCAAGTCGAGCGGAGATGAGGTGCTTG CACCTTATCTTAGCGGCGGACGGGTGAG TAATGCTTAGGAATCTGCCTATTAGTGGG GGACAACATTCCGAAAGGAATGCTAATA CCGCATACGTCCTACGGGAGAAAGCAGG GGATCTTCGGACCTTGCGCTAATAGATG AGCCTAAGTCGGATTAGCTAGTTGGTGG GGTAAAGGCCTACCAAGGCGACGATCTG TAGCGGGTCTGAGAGGATGATCCGCCAC ACTGGGACTGAGACACGGCCCAGACTCC TACGGGAGGCAGCAGTGGGGAATATTG GACAATGGGGGAACCCTGATCCAGCCA TGCCGCGTGTGTGAAGAAGGCCTTATGG TTGTAAAGCACTTTAAGCGAGGAGGAGG CTACTGAGACTAATACTCTTGGATAGTGG ACGTTACTCGCAGAATAAGCACCGGCTA ACTCTGTG | AM410704 | 100 | Bacteria;;Proteobacteria;; Gammaproteobacteria;; Pseudomonadales;; Moraxellaceae;; Acinetobacter;Acinetobacter junii;; LMG 998-AM410704(T) |
| IOFBYRO01A8KAW | TATTAGTGGGGGACAACATTCCGAAAGG AATGCTAATCCGCATACGTCCTACGGGA GAAAGCAGGGGACCTTCGGGCCTTGCGC TAATAGATGAGCCTAAGTCGGATTAGCT AGTTGGTGGGGTAAAGGCCTACCAAGGC GACGATCTGTAGCGGGTCTGAGAGGATG ATCCGCCACACTGGGACTGAGACACGGC CCAGACTCCTACGGGAGGCAGCAGTGG GGAATATTGGACAATGGGGGAACCCTG ATCCAGCCATGCCGCGTGTGTGAAGAAG GCCTTATGGTTGTAAAGCACTTTAAGCGA GGAGGAGGCTACTAGTATTAATACTACTG GATAGTGGACGTTACTCGCAGAATAAGC ACCGGCTAACTCTGTG | AKIQ01000085 | 100 | Bacteria;;Proteobacteria;; Gammaproteobacteria;; Pseudomonadales;; Moraxellaceae;; Acinetobacter;Acinetobacter venetianus;;RAG-1- AKIQ01000085(T) |

TABLE 6

Firmicutes

| Raw data Seq Name | Sequence | Hit accession | Similarity | Taxonomic assignment |
|---|---|---|---|---|
| IOFBYRO01ANZSO | GGCGGCGTGCCTAATACATGCAAGTAGA ACGCTGAAGCTTGGTGCTTGCACCGAGC GGATGAGTTGCGAACGGGTGAGTAACGC GTAGGTAACCTGCCTCTTAGCGGGGGAT AACTATTGGAAACGATAGCTAATACAGCA TAAAAGTCGATATCGCATGATATTGATTT GAAAGGTGCAATTGCATCACTAAGAGAT GGACCTGCGTTGTATTAGCTAGTTGGTG AGGTAACGGCTCACCAAGGCGACGATAC ATAGCCGACCTGAGAGGGTGATCGGCCA CACTGGGACTGAGACACGGCCCAGACTC CTACGGGAGGCAGCAGTAGGGAATCTTC GGCAATGGGGGCAACCCTGACCGAGCA ACGCCGCGTGAGTGAAGAAGGTTTTTCG GATCGTAAAGCTCTGTTGTAAGAGAAGAA CGAGTGTGAGAGTGGAAAGTTCACACTG TGACGGTAACTTACCAGAAAGGGACGGC TAACTACGTG | ADVN01000004 | 97.53 | Bacteria;;Firmicutes;; Bacilli;;Lactobacillales;; Streptococcaceae;; Streptococcus;Streptococcus parasanguinis;;ATCC 15912- ADVN01000004(T) |

TABLE 7

| | Bacteroidetes | | | |
|---|---|---|---|---|
| Raw data Seq Name | Sequence | Hit accession | Similarity | Taxonomic assignment |
| IOFBYRO01BUV34 | TGAACGCTAGCGGCAGGCTTAATACATG CAAGTCGTGGGGCAGCACAGAATAGCAA TATTTGGGTGGCGACCGGCAAACGGGTG CGGAACACGTACACAACCTTCCGATAAG TGGGGGATAGCCCAGAGAAATTTGGATT AATACCCCGTAACATATAGAGATGGCATC GTCTTTATATTATAGCTTCGGTGCTTATT GATGGGTGTGCGTCTGATTAGGTAGTTG GCGGGGTAACGGCCCACCAAGCCTACG ATCAGTAGCTGATGTGAGAGCATGATCA GCCACACGGGCACTGAGACACGGGCCC GACTCCTACGGGAGGCAGCAGTAAGGAA TATTGGACAATGGGCGCAAGCCTGATCC AGCCATGCCGCGTGAAGGATGAATGTCC TCTGGATTGTAAACTTCTTTTATTTGGGA CGAAAAAGAGCATTCTTGCTCACTTGACG GTACCAAGTGAATAAGCACCGGCTAACT CCGTG | 4P004046 | 99.79 | Bacteria;;;Bacteroidetes;; Sphingobacteria;; Sphingobacteriales;; Chitinophagaceae;; 4P004046_g;4P004046_s;; 4P004046 |
| IOFBYRO01AEZDS | GATGAACGCTAGCGATAGGCCTAACACA TGCAAGTCGAGGGGCAGCACATGAAGTA GCAATACTGATGGTGGCGACCGGCGCA CGGGTGAGTAACACGTATGCAACCTACC TTCAACAGGAGAATAACCCGTCGAAAGA CGGACTAATACTCCATAACACAGGGATC CCACATGGGAATATTGTTAAAGATTTAT CGGTTGAAGATGGGCATGCGCTCCATTA GCTAGTTGGTGAGGTAACGGCTCACCAA GGCAACGATGGATAGGGGAACTGAGAG GTTTATCCCCCACACTGGTACTGAGACA CGGACCAGACTCCTACGGGAGGCAGCA GTGAGGAATATTGGTCAATGGAGGCAAC TCTGAACCAGCCACGTCGCGTGAAGGAT GACGGCCCTACGGGTTGTAAACTTCTTTT GTAAGGGAATAAAGTTAGTTACGTGTAAC TATTTGCATGTACCTTACGAATAAGGATC GGCTAACTCCGTG | FJ672469 | 97.34 | Bacteria;;;Bacteroidetes;; Bacteroidia;;Bacteroidales;; Porphyromonadaceae;; AB243818_g;FJ672469_s;; FJ672469 |
| IOFBYRO01BP52Z | GATGAACGCTAGCGATAGGCCTAACACA TGCAAGTCGAGGGGCAGCACATGAAGTA GCAATACTGATGGTGGCGACCGGCGCA CGGGTGAGTAACACGTATGCAACCTACC TTCAACAGGAGAATAACCCGTCGAAAGA CGGACTAATACTCCATAACACAGGGATC CCACATGGGAATATTGTTAAAGATTTAT CGGTTGAAGATGGGCATGCGCTCCATTA GCTAGTTGGTGAGGTAACGGCTCACCAA GGCAACGATGGATAGGGGAACTGAGAG GTTTATCCCCCACACTGGTACTGAGACA CGGACCAGACTCCTACGGGAGGCAGCA GTGAGGAATATTGGTCAATGGAGGCAAC TCTGAACCAGCCACGTCGCGTGAAGGAT GACGGCCCTACGGGTTGTAAACTTCTTTT GTAAGGGAATAAAGTTAGTTACGTGTAAC TATTTGCATGTACCTTACGAATAAGGATC GGCTAACTCCGTG | FJ672469 | 97.34 | Bacteria;;;Bacteroidetes;; Bacteroidia;;Bacteroidales;; Porphyromonadaceae;; AB243818_g;FJ672469_s;; FJ672469 |
| IOFBYRO01BBMIP | TGAACGCTAGCGGCAGGCTTAATACATG CAAGTCGTGGGGCAGCACAGAATAGCAA TATTTGGGTGGCGACCGGCAAACGGGTG CGGAACACGTACACAACCTTCCGATAAG TGGGGGATAGCCCAGAGAAATTTGGATT AATACCCCGTAACATATAGAGATGGCATC GTCTTTATATTATAGCTTCGGTGCTTATT GATGGGTGTGCGTCTGATTAGGTAGTTG GCGGGGTAACGGCCCACCAAGCCTACG ATCAGTAGCTGATGTGAGAGCATGATCA GCCACACGGGCACTGAGACACGGGCCC GACTCCTACGGGAGGCAGCAGTAAGGAA TATTGGACAATGGGCGCAAGCCTGATCC AGCCATGCCGCGTGAAGGATGAATGTCC TCTGGATTGTAAACTTCTTTTATTTGGGA CGAAAAAGAGCATTCTTGCTCACTTGAC GGTACCAAGTGAATAAGCACCGGCTAAC TCCGTG | 4P004046 | 99.79 | Bacteria;;;Bacteroidetes;; Sphingobacteria;; Sphingobacteriales;; Chitinophagaceae;; 4P004046_g;4P004046_s;; 4P004046 |

TABLE 7-continued

Bacteroidetes

| Raw data Seq Name | Sequence | Hit accession | Similarity | Taxonomic assignment |
|---|---|---|---|---|
| IOFBYRO01BBHTW | ATGGACGCTAGCGGCAGGCTTAATACAT GCAAGTCGTGGGGCAGCACAGAATAGCA ATATTGGGTGGCGACCGGCAAACGGGT GCGGAACACGTACACAACCTTCCGATAA GTGGGGGATAGCCCAGAGAAATTTGGAT TAATACCCCGTAACATATAGAGATGGCAT CGTCTTTATATTATAGCTTCGGCGCTTAT TGATGGGTGTGCGTCTAATTAGGTAGTT GGCGGGGTAACGGCCCACCAAGCCTAC GATCAGTAGCTGATGTGAGAGCATGATC AGCCACACGGGCACTGAGACACGGGCC CGACTCCTACGGGAGGCAGCAGTAAGG AATATTGGACAATGGGCGCAAGCCTGAT CCAGCCATGCCGCGTGAAGGATGAATGT CCTCTGGATTGTAAACTTCTTTTATTTGG GACGAAAAAAGAGCATTCTTGCTCACTTG ACGGTACCAAGTGAATAAGCACCGGCTA ACTCCGTG | 4P004046 | 99.58 | Bacteria;;;Bacteroidetes;; Sphingobacteria;; Sphingobacteriales;; Chitinophagaceae;; 4P004046_g;4P004046_s;; 4P004046 |
| IOFBYRO01BQCEI | GATGAACGCTAGCGATAGGCCTAACACA TGCAAGTCGAAGGGGCAGCACATGAAGT AGCAATACTGATGGTGGCGACCGGCGCA CGGGTGAGTAACACGTATGCAACCTACC TTCAACAGGAGAATAACCCGTCGAAAGA CGGACTAATACTCCATAACAGGGGATC CCACATGGGAATATTGTTAAAGAGTTTA TCGGTTGAAGATGGGCATGCGCTCCATT AGCTAGTTGGTGAGGTAACGGCTCACCA AGGCAACGATGGATAGGGGAACTGAGA GGTTTATCCCCCACACTGGTACTGAGAC ACGGACCAGACTCCTACGGGAGGCAGC AGTGAGGAATATTGGTCAATGGAGGCAA CTCTGAACCAGCCACGTCGCGTGAAGGA TGACGGCCCTACGGGTTGTAAACTTCTTT TGTAAGGGAATAAAGTTAGTTACGTGTAA CTATTTGCATGTACCTTACGAATAAGGAT CGGCTAACTCCGTG | FJ672469 | 97.34 | Bacteria;;;Bacteroidetes;; Bacteroidia;;Bacteroidales;; Porphyromonadaceae;; AB243818_g;FJ672469_s;; FJ672469 |
| IOFBYRO01CGIIX | ATGAACGCTAGCGGCAGGCTTAATACAT GCAAGTCGAGGGGCAGCACGGTATAGC AATATATGGGTGGCGACCGGCAAACGGG TGCGGAACACGTACACAACCTTCCGGTG AGCGGGGGATAGCCCAGAGAAATTTGGA TTAATACCCCATACTATAATGATCAGGCA TCTGGTTATTATCAAAGGCTTCGGCCGCT TATTGATGGGTGTGCGTCTGATTAGGTA GTTGGCGGGGTAGAGGCCCACCAAGCC TACGATCAGTAGCTGATGTGAGAGCATG ATCAGCCACACGGGCACTGAGACACGGG CCCGACTCCTACGGGAGGCAGCAGTAA GGAATATTGGACAATGGACGCAAGTCTG ATCCAGCCATGCTGCGTGAAGGATGAAT GCCCTCTGGGTTGTAAACTTCTTTTACAG GGGAAGAAAGTTATCTTTTTTAGGATATT TGACGGTACCCTATGAATAAGCACCGGC TAACTCCGTG | FN665659 | 97.8 | Bacteria;;;Bacteroidetes;; Sphingobacteria;; Sphingobacteriales;; Chitinophagaceae;; Hydrotalea;Hydrotalea flava;; CCUG 51397-FN665659(T) |
| IOFBYRO01BUV35 | TGAACGCTAGCGGCAGGCTTAATACATG CAAGTCGTGGGCAGCACAGAATAGCAA TATTTGGGTGGCGACCGGCAAACGGGTG CGGAACACGTACACAACCTTCCGATAAG TGGGGGATAGCCCAGAGAAATTTGGATT AATACCCCGTAACATATAGAGATGGCATC GTCTTTATATTATAGCTTCGGTGCTTATT GATGGGTGTGCGTCTGATTAGGTAGTTG GCGGGGTAACGGCCCACCAAGCCTACG ATCAGTAGCTGATGTGAGAGCATGATCA GCCACACGGGCACTGAGACACGGGCCC GACTCCTACGGGAGGCAGCAGTAAGGAA TATTGGACAATGGGCGCAAGCCTGATCC AGCCATGCCGCGTGAAGGATGAATGTCC | 4P004047 | 99.24906689 | Bacteria;;;Bacteroidetes;; Sphingobacteria;; Sphingobacteriales;; Chitinophagaceae;; 4P004046_g;4P004046_s;; 4P004047 |

TABLE 7-continued

| | Bacteroidetes | | | |
|---|---|---|---|---|
| Raw data Seq Name | Sequence | Hit accession | Similarity | Taxonomic assignment |
| | TCTGGATTGTAAACTTCTTTTATTTGGGA CGAAAAAGAGCATTCTTGCTCACTTGACG GTACCAAGTGAATAAGCACCGGCTAACT CCGTG | | | |

TABLE 8

| | Streptophyta | | | |
|---|---|---|---|---|
| Raw data Seq Name | Sequence | Hit accession | Similarity | Taxonomic assignment |
| IOFBYRO01BVMU5 | GATGAACGCTGGCGGCATGCTTAACACA TGCAAGTCGGACGGGAAGTGGTGTTTCC AGTGGCGGACGGGTGAGTAACGCGTAA GAACCTGCCCTTGGGAGGGGAACAACA GCTGGAAACGGCTGCTAATACCCCGTAG GCTGAGGAGCAAAAGGAGGAATCCGCC CGAGGAGGGGCTCGCGTCTGATTAGCTA GTTGGTGAGGCAATAGCTTACCAAGGCG ATGATCAGTAGCTGGTCCGAGAGGATGA TCAGCCACACTGGGACTGAGACACGGCC CAGACTCCTACGGGAGGCAGCAGTGGG GAATTTTCCGCAATGGGCGAAAGCCTGA CGGAGCAATGCCGCGTGGAGGTAGAAG GCCCACGGGTCGTGAACTTCTTTTCCCG GAGAAGAAGCAATGACGGTATCTGGGGA ATAAGCATCGGCTAACTCTGTG | CAAP02016081 | 100 | Eukarya;Viridiplantae;; Streptophyta;; eudicotyledons;;core eudicotyledons;; Vitaceae;;*Vitis*;*Vitis vinifera*;;CAAP02016081 |
| IOFBYRO01DG9Y3 | GATGAACGCTGGCGGCATGCTTAACACA TGCAAGTCGGACGGGAAGTGGTGTTTCC AGTGGCGGACGGGTGAGTAACGCGTAA GAACCTGCCCTTGGGAGGGGAACAACA GCTGGAAACGGCTGCTAATACCCCGTAG GCTGAGGAGCAAAAGGAGGAATCCGCC CGAGGAGGGGCTCGCGTCTGATTAGCTA GTTGGTGAGGCAATAGCTTACCAAGGCG ATGATCAGTAGCTGGTCCGAGAGGATGA TCAGCCACACTGGGACTGAGACACGGCC CAGACTCCTACGGGAGGCAGCAGTGGG GAATTTTCCGCAATGGGCGAAAGCCTGA CGGAGCAATGCCGCGTGGAGGTAGAAG GCCCACGGGTCGTGAACTTCTTTTCCCG GAGAAGAAGCAATGACGGTATCTGGGGA ATAAGCATCGGCTAACTCTGTG | CAAP02016081 | 100 | Eukarya;Viridiplantae;; Streptophyta;; eudicotyledons;;core eudicotyledons;; Vitaceae;;*Vitis*;*Vitis vinifera*;;CAAP02016081 |
| IOFBYRO01BVXH2 | GATGAACGCTGGCGGCATGCTTAACACA TGCAAGTCGGACGGGAAGTGGTGTTTCC AGTGGCGGACGGGTGAGTAACGCGTAA GAACCTGCCCTTGGGAGGGGAACAACA GCTGGAAACGGCTGCTAATACCCCGTAG GCTGAGGAGCAAAAGGAGGAATCCGCC CGAGGAGGGGCTCGCGTCTGATTAGCTA GTTGGTGAGGCAATAGCTTACCAAGGCG ATGATCAGTAGCTGGTCCGAGAGGATGA TCAGCCACACTGGGACTGAGACACGGCC CAGACTCCTACGGGAGGCAGCAGTGGG GAATTTTCCGCAATGGGCGAAAGCCTGA CGGAGCAATGCCGCGTGGAGGTAGAAG GCCCACGGGTCGTGAACTTCTTTTCCCG GAGAAGAAGCAATGACGGTATCTGGGGA ATAAGCATCGGCTAACTCTGTG | CAAP02016081 | 100 | Eukarya;Viridiplantae;; Streptophyta;; eudieotyledons;;core eudieotyledons;; Vitaceae;;*Vitis*;*Vitis vinifera*;;CAAP02016081 |
| IOFBYRO01CVD3E | GATGAACGCTGGCGGCATGCTTAACACA TGCAAGTCGGACGGGAAGTGGTGTTTCC AGTGGCGGACGGGTGAGTAACGCGTAA GAACCTGCCCTTGGGAGGGGAACAACA GCTGGAAACGGCTGCTAATACCCCGTAG GCTGAGGAGCAAAAGGAGGAATCCGCC CGAGGAGGGGCTCGCGTCTGATTAGCTA GTTGGTGGGGCAATAGCTTACCAAGGCG ATGATCAGTAGCTGGTCCGAGAGGATGA | CAAP02016081 | 99.77 | Eukarya;Viridiplantae;; Streptophyta;; eudieotyledons;;core eudieotyledons;; Vitaceae;;*Vitis*;*Vitis vinifera*;;CAAP02016081 |

TABLE 8-continued

Streptophyta

| Raw data Seq Name | Sequence | Hit accession | Similarity | Taxonomic assignment |
|---|---|---|---|---|
| | TCAGCCACACTGGGACTGAGACACGGCC | | | |
| | CAGACTCCTACGGGAGGCAGCAGTGGG | | | |
| | GAATTTTCCGCAATGGGCGAAAGCCTGA | | | |
| | CGGAGCAATGCCGCGTGGAGGTAGAAG | | | |
| | GCCCACGGGTCGTGAACTTCTTTTCCCG | | | |
| | GAGAAGAAGCAATGACGGTATCTGGGGA | | | |
| | ATAAGCATCGGCTAACTCTGTG | | | |

(2) Semen-Derived Luterials

The semen-derived luterials obtained in Example 2 were subjected to gDNA extraction, PCR amplification and sequencing according to the above-described method. FIG. 25 shows bacterial homology of luterial DNA as determined by 16S rRNA sequencing of luterials derived from semen in both normal condition and a fatigue and disease condition (sperm pH: 7.0 or less). The analysis was performed with the luterials of various sizes ((a): 100 nm or less, (b): 100-200 nm, and (d) 400-800 nm).

The normal semen-derived luterials showed homology with the genes derived from Proteobacteria, Firmicutes and Bacteroidetes, like the blood-derived luterials. Particularly, the luterials showed homology with the Chordata-derived gene.

Luterial DNA derived from semen in abnormal acidic conditions showed homology with the Streptophyta-derived gene.

(7) Measurement of ATP Content 10 mL of each of four media, including a control, luterial, luterial with SSH (12 hr) and luterial with SSF (12 hr), was placed in a tube, and glucose (100 mg/mL) and ADP substrate (1 mM) were added thereto, followed by culture in water bath at 37° C. At 30-min intervals after the start of the culture, 100 µl of a sample was collected, placed in a tube, and diluted 10-fold with 900 µl of distilled water. Then, 10 µl of the sample was transferred into a fresh tube, and 100 µl of luciferase reagent contained in the ATP kit was added thereto, and measurement was immediately performed five times using a luminometer.

As shown in FIG. 18, the media containing luterial showed an increase in the ATP concentration compared to the control media without luterial. Such results suggest that the luterial has the ability to produce ATP. In comparing the results between SSH and SSF media, the ATP concentration in the SSF-added group was higher than that in the SSH-added group (FIG. 18).

Figure 22:
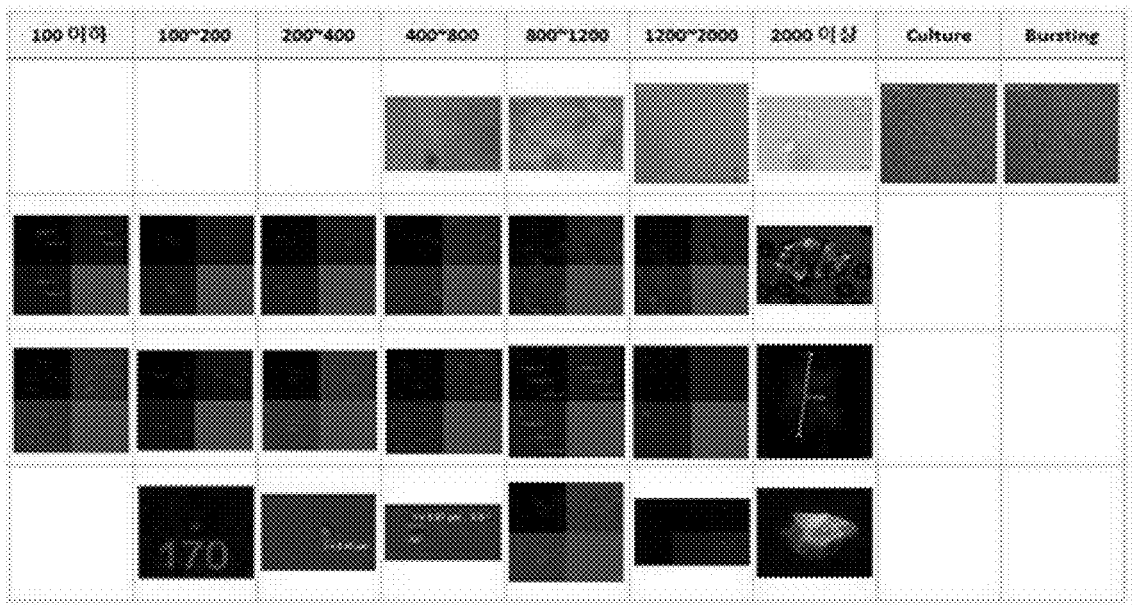
FIG. 22 depicts confocal laser scanning microscope images showing the change in size of luterial caused by culture.

Example 4: Culture of Luterials (1) Among luterials obtained in Example 1, luterials having a size of about 50-200 nm were irradiated with IR light after addition of PBS, and then cultured at 18 to 30° C. for about 3 hours. At about 1-hour intervals immediately after irradiation with IR light, the size of the luterials was measured with a microscope. After about 1-6 hours, luterials having a size of about 200 nm before culture grew to a size of about 500 nm. Thus, when water was added to blood-derived luterials which were then cultured at 18 to 30° C. under irradiation with IR light, the luterials could grow to a size of about 500 nm. Consistently, when luterials were additionally cultured, they grew to a size of several hundreds of 1 µm and did also burst during the additional culture (FIG. 22).

(2) Among luterials obtained in Example 1, luterials having a size of about 400-800 nm were irradiated with IR light after addition of PBS, and then cultured at 18 to 30° C. for about 3 hours. At about 1-hour intervals immediately after irradiation with IR light, the size and status of luterials were measured with a microscope. After about 1-6 hours, it was shown that luterials having a size of about 400-800 nm before culture underwent fission without growth.

Figure 23:
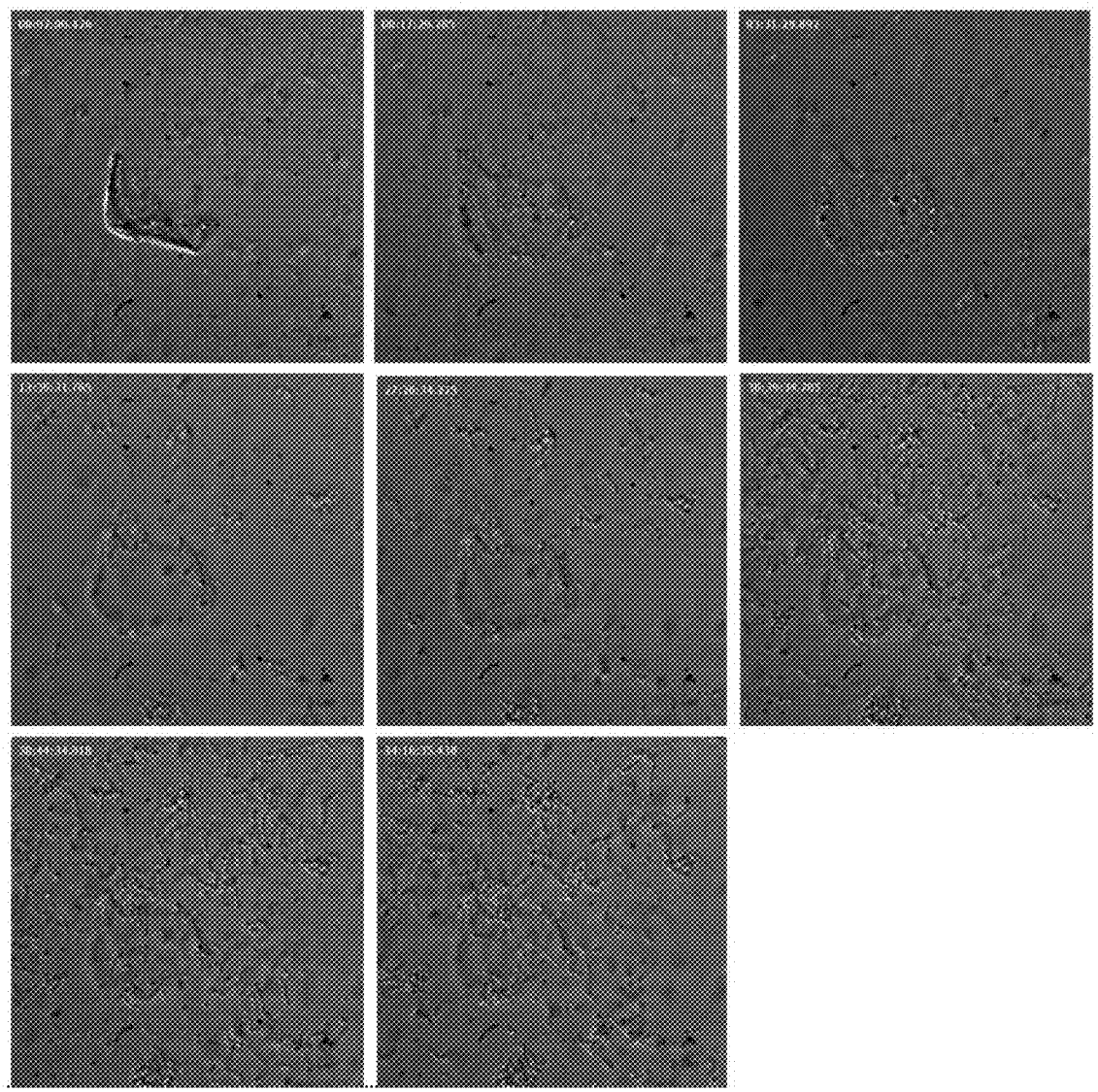
FIG. 23 depicts images showing the change in morphology and size of luterial caused by culture.

In addition, it was observed that, when mutant luterials having a size of 800 nm or more were further cultured, they changed to mutant luterials that are seen in the blood of cancer patients (FIG. 23).

Example 5: Anticancer Effect of Luterials

In order to measure inhibitory effects of luterials on the growth of two ovarian cell lines (SKOV3 and A2780), a yellow tetrazolium MTT (3-(4,5-dimethylthiazolyl-2)-2,5-diphenyltetrazolium bromide) assay was performed. The MTT assay is a method for measuring the growth of living cells, and is based on the principle that dehydrogenase in mitochondria of living cells produces violet formazan when the yellow water-soluble substance MTT is added. The production of violet formazan is known to be substantially proportional to the number of living cells having metabolic activity, and thus can be very effective in measuring the growth and differentiation of cells.

Specifically, 100 µl of cultured cancer cells were added to a 96-well plate at a concentration of $5\times10^4$ cells/ml and cultured in a humidified incubator (5% carbon and 95% oxygen) at 37° C. for 24 hours, and then treated with various concentrations of luterials having a size of 100-800 nm. After 48 hours of culture, 15 µl of a solution of MTT (5 mg/ml) in phosphate buffered saline (PBS) was added to each well, followed by culture for 4 hours. After the formation of formazan was confirmed, the medium was completely removed, and 100 µl of dimethyl sulfoxide (DMSO) was added to each well in order to dissolve formazan formed at the well bottom. Thereafter, the absorbance at 560 nm was measured using a microplate reader (GEMINI, Stratec Biomedical), and the inhibition rate of cell growth by luterials relative to 100% of the control cells was calculated.

Figure 27:
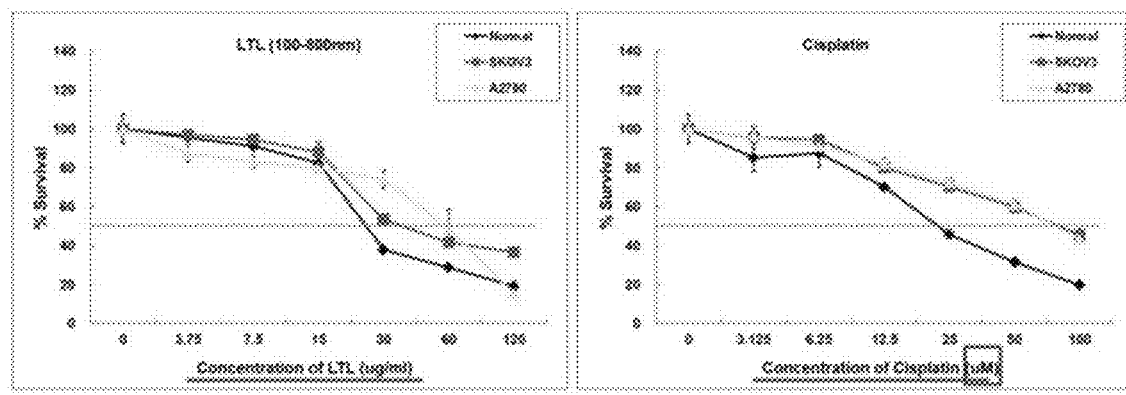
FIG. 27 shows cell viability measured by an MTT assay after treating ovarian cancer cell lines (SKOV3 and A2780) with varying concentrations of luterials having a size of 100-800 nm and the commercially available anticancer drug cisplatin.

As a result, the $IC_{50}$ values of luterials for the SKOV3 and A2780 cell lines were 30 µg/ml and 60 µg/ml, respectively. The $IC_{50}$ value of the commercially available anticancer drug cisplatin was 100 µM (FIG. 27). Luterials showed stronger cytotoxicity than the positive control drug for the two ovarian cancer cell lines, and showed cytotoxicity similar to that of the positive control drug for normal ovarian cells.

INDUSTRIAL APPLICABILITY

As described above, according to the present invention, the unidentified nano-sized particle luterial present in the body fluid of patients or normal persons can be effectively isolated, and the isolated luterial can be cultured so as to grow to a certain size. As such, luterial is useful for the diagnosis and treatment of disease. In addition, luterial shows a strong anticancer effect against cancer cell lines, and thus is useful as an anticancer agent.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for isolating luterial, comprising the steps of:
   (a) removing platelet and blood-derived substances having a size greater than that of platelet from blood, and passing blood in which platelet and blood-derived substances have been removed through a filter having a pore size of 0.8-1.2 μm;
   (b) centrifuging the filtered solution at 120,000-500,000 g to remove general microvesicles including exosomes collected in pellets and collect a supernatant;
   (c) irradiating light to the supernatant obtained by the centrifugation and isolating fluorescent and mobile particles from the supernatant obtained by the centrifugation.

2. The method of claim 1, wherein the blood is derived from mammals.

3. The method of claim 2, wherein the blood is derived from human.

4. The method of claim 1, wherein luterial is classified according to size into 50-200 nm, 200-400 nm, 400-600 nm, 600-800 nm, and 800-1,000 nm by the sequential use of 200 nm, 400 nm, 600 nm, 800 nm, and 1000 nm sized filters.

5. The method of claim 1, wherein luterial is positively stained by Janus green B, Rhodamine 123, Mitotracker, Acridine Orange, or DAPI.

* * * * *

UNITED STATES PATENT AND TRADEMARK OFFICE
CERTIFICATE OF CORRECTION

PATENT NO. : 10,624,926 B2
APPLICATION NO. : 15/109114
DATED : April 21, 2020
INVENTOR(S) : Choi et al.

It is certified that error appears in the above-identified patent and that said Letters Patent is hereby corrected as shown below:

In the Specification

Column 7, Line 63: "sternness" should be -- stemness --.

Signed and Sealed this
Ninth Day of June, 2020

Andrei Iancu
*Director of the United States Patent and Trademark Office*